US011089972B2

(12) United States Patent
Sutin et al.

(10) Patent No.: US 11,089,972 B2
(45) Date of Patent: Aug. 17, 2021

(54) SYSTEM AND METHOD FOR NON-INVASIVELY MONITORING INTRACRANIAL PRESSURE

(71) Applicant: The General Hospital Corporation, Boston, MA (US)

(72) Inventors: Jason Sutin, Cambridge, MA (US); Maria Angela Franceschini, Winchester, MA (US); David Boas, Winchester, MA (US)

(73) Assignee: The General Hospital Corporation, Boston, MA (US)

( * ) Notice: Subject to any disclaimer, the term of this patent is extended or adjusted under 35 U.S.C. 154(b) by 265 days.

(21) Appl. No.: 15/565,044

(22) PCT Filed: Apr. 11, 2016

(86) PCT No.: PCT/US2016/026920
§ 371 (c)(1),
(2) Date: Oct. 6, 2017

(87) PCT Pub. No.: WO2016/164891
PCT Pub. Date: Oct. 13, 2016

(65) Prior Publication Data
US 2018/0103861 A1 Apr. 19, 2018

Related U.S. Application Data

(60) Provisional application No. 62/145,087, filed on Apr. 9, 2015.

(51) Int. Cl.
A61B 5/00 (2006.01)
A61B 5/0205 (2006.01)
(Continued)

(52) U.S. Cl.
CPC .......... *A61B 5/031* (2013.01); *A61B 5/0075* (2013.01); *A61B 5/0205* (2013.01); *A61B 5/029* (2013.01);
(Continued)

(58) Field of Classification Search
CPC ..... A61B 5/031; A61B 5/7246; A61B 5/6814; A61B 5/0261; A61B 5/0205
See application file for complete search history.

(56) References Cited

U.S. PATENT DOCUMENTS

2005/0015009 A1* 1/2005 Mourad ............... A61B 5/7267
600/438
2008/0004531 A1 1/2008 Carp
(Continued)

FOREIGN PATENT DOCUMENTS

CN 1044899 8/1990
CN 101720205 6/2010
(Continued)

OTHER PUBLICATIONS

Varsos GV, de Riva N, Smielewski P, Pickard J, Brady K, Reinhard M et al. Critical closing pressure during intracranial pressure plateau waves. Neurocrit Care; 18 (3): 341-348. (Year: 2013).*
(Continued)

Primary Examiner — Bill Thomson
Assistant Examiner — Amal Aly Farag
(74) Attorney, Agent, or Firm — Quarles & Brady LLP

(57) ABSTRACT

A system and method for non-invasively monitoring intracranial pressure are provided. In some aspects, the method comprises acquiring diffuse correlation spectroscopy data at a temporal resolution greater than a pulsatile frequency of cerebral blood flow of a subject using one or more optical sensors placed about a subject, and determining a pulsatile cerebral blood flow using the acquired data, The method also (Continued)

includes correlating the determined pulsatile cerebral blood flow with physiological data acquired from the subject, and estimating an intracranial pressure based on the correlation. The method further includes generating a report indicative of the estimated intracranial pressure.

21 Claims, 16 Drawing Sheets

(51) Int. Cl.
| | |
|---|---|
| A61B 5/026 | (2006.01) |
| A61B 5/029 | (2006.01) |
| A61B 5/03 | (2006.01) |
| A61B 5/0402 | (2006.01) |
| A61B 5/0476 | (2006.01) |
| A61B 5/318 | (2021.01) |
| A61B 5/369 | (2021.01) |
| A61B 5/021 | (2006.01) |
| A61B 5/08 | (2006.01) |
| A61B 5/145 | (2006.01) |
| A61B 5/1455 | (2006.01) |

(52) U.S. Cl.
CPC ............ *A61B 5/0261* (2013.01); *A61B 5/318* (2021.01); *A61B 5/369* (2021.01); *A61B 5/6814* (2013.01); *A61B 5/7246* (2013.01); *A61B 5/7278* (2013.01); *A61B 5/021* (2013.01); *A61B 5/08* (2013.01); *A61B 5/14546* (2013.01); *A61B 5/14552* (2013.01); *A61B 2562/0238* (2013.01)

(56) References Cited

U.S. PATENT DOCUMENTS

| | | | |
|---|---|---|---|
| 2009/0062685 | A1 | 3/2009 | Bergethon et al. |
| 2009/0149751 | A1* | 6/2009 | Mourad .................. A61B 5/031 600/438 |
| 2010/0168586 | A1 | 7/2010 | Hillman et al. |
| 2010/0241006 | A1 | 9/2010 | Choi et al. |
| 2010/0268096 | A1 | 10/2010 | Berka et al. |
| 2013/0172703 | A1 | 7/2013 | Dixon et al. |
| 2014/0052006 | A1* | 2/2014 | Lee ...................... A61B 5/7278 600/479 |
| 2014/0316218 | A1 | 10/2014 | Purdon |

FOREIGN PATENT DOCUMENTS

| | | |
|---|---|---|
| CN | 201564473 U | 9/2010 |
| KR | 10-1008041 B1 | 1/2011 |
| WO | 2002043564 B2 | 6/2002 |
| WO | WO 2007097702 A1 | 8/2007 |
| WO | 2015022583 | 2/2015 |

OTHER PUBLICATIONS

Czosnyka, M., Smielewski, P., Piechnik, S., Al-Rawi, P.G., Kirkpatrick, P.J., Matta, B.F., Pickard, J.D., "Critical closing pressure in cerebrovascular circulation." J Neurol Neurosurg Psych, 66, pp. 606-611 (Year: 1999).*
International Search Report and Written Opinion for International Application No. PCT/US2016/026920 dated Jul. 7, 2016, 15 pages.
Franceschini, M. A. et al. The effect of different anesthetics on neurovascular coupling. Neuroimage 51, 1367-1377 (2010).
Franceschini, M. A., et al. Noninvasive optical method of measuring tissue and arterial saturation: an application to absolute pulse oximetry of the brain. Opt Lett 24, 829-831 (1999).
Gagnon, L. et al. Double-layer estimation of intra- and extracerebral hemoglobin concentration with a time-resolved system. J Biomed Opt 13, 054019 (2008).
Grubb, R. L., et al. The effects of changes in PaCO2 on cerebral blood volume, blood flow, and vascular mean transit time. Stroke 5, 630-639 (1974).
Guarracino, F. Cerebral monitoring during cardiovascular surgery. Current Opinion in Anaesthesiology 21, 50-54 (2008).
Guillaume, J. et al. [Continuous intracranial manometry; importance of the method and first results]. Rev. Neurol. (Paris) 84, 131-142 (1951).
Gurley, K. et al. "Noninvasive optical quantification of absolute blood flow, blood oxygenation, and oxygen consumption rate in exercising skeletal muscle." Journal of biomedical optics 17.7 (2012): 075010.
Holloway, K. L. et al. Ventriculostomy infections: the effect of monitoring duration and catheter exchange in 584 patients. J Neurosurg 85, 419-424 (1996).
Ijichi, S. et al. Developmental changes of optical properties in neonates determined by near-infrared time-resolved spectroscopy. Pediatr Res 58, 568-573 (2005).
International Search Report and Written Opinion for International Application No. PCT/US2016/026925 dated Jul. 6, 2016, 11 pages.
Irwin, D. et al. Influences of tissue absorption and scattering on diffuse correlation spectroscopy blood flow measurements. Biomed Opt Express 2, 1969-1985 (2011).
Ito, H., et al. Changes in human cerebral blood flow and cerebral blood volume during hypercapnia and hypocapnia measured by positron emission tomography. J Cereb Blood Flow Metab 23, 665-670 (2003).
Jain, V. et al. Cerebral oxygen metabolism in neonates with congenital heart disease quantified by MRI and optics. J Cereb Blood Flow Metab (2013). doi:10.1038/jcbfm.2013.214.
Jiang, L., et al. High-power DBR laser diodes grown in a single epitaxial step. in SPIE OPTO: Integrated Optoelectronic Devices (Belyanin, A. A. & Smowton, P. M.) 7230, 72301F-72301F-9 (SPIE, 2009).
Jones, M., et al. Changes in blood flow, oxygenation, and volume following extended stimulation of rodent barrel cortex. Neuroimage 15, 474-487 (2002).
Kangara, J. C. B. et al. Design and construction of cost-effective tapered amplifier systems for laser cooling and trapping experiments. Am. J. Phys. 82, 805-817 (2014).
Kienle, A. et al. Improved solutions of the steady-state and the time-resolved diffusion equations for reflectance from a semi-infinite turbid medium. J Opt Soc Am A 14, 246-254 (1997).
Kim, M. N. et al. Continuous Optical Monitoring of Cerebral Hemodynamics During Head-of-Bed Manipulation in Brain-Injured Adults. Neurocrit Care (2013). doi:10.1007/s12028-013-9849-7.
Kim, M. N. et al. Noninvasive measurement of cerebral blood flow and blood oxygenation using near-infrared and diffuse correlation spectroscopies in critically brain-injured adults. Neurocrit Care 12, 173-180 (2010).
Kirkpatrick, P. J., et al. Continuous monitoring of cortical perfusion by laser Doppler flowmetry in ventilated patients with head injury. J. Neurol. Neurosurg. Psychiatr. 57, 1382-1388 (1994).
Kirkpatrick, PJ, et al. "Near-infrared spectroscopy use in patients with head injury." Journal of neurosurgery 83.6 (1995): 963-970.
Klingelhöfer, J. et al. Doppler CO2 test as an indicator of cerebral vasoreactivity and prognosis in severe intracranial hemorrhages. Stroke 23, 962-966 (1992).
Li, J., et al. "Pulsation-resolved deep tissue dynamics measured with diffusing-wave spectroscopy." Optics express 14.17 (2006): 7841-7851.
Li, Z., et al. "Calibration of diffuse correlation spectroscopy blood flow index with venous-occlusion diffuse optical spectroscopy in skeletal muscle." Journal of biomedical optics 20.12 (2015): 125005.
Liebert, A. et al. Evaluation of optical properties of highly scattering media by moments of distributions of times of flight of photons. Appl Opt 42, 5785-5792 (2003).
Liebert, A., et al. Fiber dispersion in time domain measurements compromising the accuracy of determination of optical properties of strongly scattering media. J Biomed Opt 8, 512-516 (2003).
Lin, P.-Y. et al. Non-invasive optical measurement of cerebral metabolism and hemodynamics in infants. J Vis Exp e4379 (2013). doi:10.3791/4379.

(56) References Cited

OTHER PUBLICATIONS

Lin, P.-Y. et al. Regional and hemispheric asymmetries of cerebral hemodynamic and oxygen metabolism in newborns. Cereb Cortex 23, 339-348 (2013).

Lynch, J. M. et al. Noninvasive optical quantification of cerebral venous oxygen saturation in humans. Acad Radiol 21, 162-167 (2014).

Maas, A. I. R., et al. Moderate and severe traumatic brain injury in adults. Lancet Neurol 7, 728-741 (2008).

Magatti, D. et al. "Fast multi-tau real-time software correlator for dynamic light scattering." Applied optics 40.24 (2001): 4011-4021.

Marzban, C. et al. A method for estimating zero-flow pressure and intracranial pressure. J Neurosurg Anesthesiol 25, 25-32 (2013).

Matcher, S. J., et al. In vivo measurements of the wavelength dependence of tissue-scattering coefficients between 760 and 900 nm measured with time-resolved spectroscopy. Appl Opt 36, 386-396 (1997).

Mesquita, R. C. et al. Direct measurement of tissue blood flow and metabolism with diffuse optics. Philos Transact A Math Phys Eng Sci 369, 4390-4406 (2011).

Mesquita, R. C. et al. Influence of probe pressure on the diffuse correlation spectroscopy blood flow signal: extra-cerebral contributions. Biomed Opt Express 4, 978-994 (2013).

Muehlschlegel, S. et al. Feasibility of NIRS in the neurointensive care unit: a pilot study in stroke using physiological oscillations. Neurocrit Care 11, 288-295 (2009).

Naqvi, J., et al. Transcranial Doppler ultrasound: a review of the physical principles and major applications in critical care. Int J Vasc Med 2013, 629378 (2013).

Ninck, M. et al. "Diffusing-wave spectroscopy with dynamic contrast variation: disentangling the effects of blood flow and extravascular tissue shearing on signals from deep tissue." Biomedical optics express 1.5 (2010): 1502-1513.

Ono, M., et al. Validation of a stand-alone near-infrared spectroscopy system for monitoring cerebral autoregulation during cardiac surgery. Anesth Analg 116, 198-204 (2013).

Panerai, R. B. The critical closing pressure of the cerebral circulation. Med Eng Phys 25, 621-632 (2003).

Patel, J., et al. Measurement of cerebral blood flow in newborn infants using near infrared spectroscopy with indocyanine green. Pediatr Res 43, 34-39 (1998).

Patterson, M. S., et al. Time resolved reflectance and transmittance for the non-invasive measurement of tissue optical properties. Appl Opt 28, 2331-2336 (1989).

Phillip, D. et al. Altered Low Frequency Oscillations of Cortical Vessels in Patients with Cerebrovascular Occlusive Disease—A NIRS Study. Front Neurol 4, 204 (2013).

Phillip, D. et al. Low frequency oscillations in cephalic vessels assessed by near infrared spectroscopy. Eur. J. Clin. Invest. 42, 1180-1188 (2012).

Pifferi, A. et al. Time-resolved diffuse reflectance using small source-detector separation and fast single-photon gating. Phys Rev Lett 100, 138101 (2008).

Poelker, M. High power gain-switched diode laser master oscillator and amplifier. Appl Phys Lett (1995).

Poulin, M. J., et al. Dynamics of the cerebral blood flow response to step changes in end-tidal PCO2 and PO2 in humans. J Appl Physiol 81, 1084-1095 (1996).

Robertson, C. S. Management of Cerebral Perfusion Pressure after Traumatic Brain Injury. Anesthesiology 95, 1513 (2001).

Roche-Labarbe, N. et al. Near-infrared spectroscopy assessment of cerebral oxygen metabolism in the developing premature brain. J Cereb Blood Flow Metab 32, 481-488 (2012).

Roche-Labarbe, N. et al. Noninvasive optical measures of CBV, StO(2), CBF index, and rCMRO(2) in human premature neonates' brains in the first six weeks of life. Hum Brain Mapp 31, 341-352 (2010).

China National Intellectual Property Administration, Notice on the First Office Action for application 201680032216.3, dated Mar. 16, 2020.

Alali, A. S. et al. Intracranial pressure monitoring in severe traumatic brain injury: results from the American College of Surgeons Trauma Quality Improvement Program. J Neurotrauma 30, 1737-1746 (2013).

Anderson, R. C. E. et al. Complications of intracranial pressure monitoring in children with head trauma. J Neurosurg 101, 53-58 (2004).

Arridge, S. R., et al. The theoretical basis for the determination of optical pathlengths in tissue: temporal and frequency analysis. Phys Med Biol 37, 1531-1560 (1992).

Auer, LM., et al. "Effect of intracranial pressure on bridging veins in rats." Journal of neurosurgery 67.2 (1987): 263-268.

Baker, W. B. et al. Probe Pressure Modulation Algorithm Reduces Extra-cerebral Contamination in Optical Measurements of Cerebral Blood Flow. in fNIRS, Society of Functional Near-Infrared Spectroscopy (2014).

Beechem, J. M. Global analysis of biochemical and biophysical data. Meth. Enzymol. 210, 37-54 (1992).

Behrens, A. et al. Transcranial Doppler Pulsatility Index. Neurosurgery 66, 1050-1057 (2010).

Bellini, T., et al. Effects of finite laser coherence in quasielastic multiple scattering. Phys. Rev., A 44, 5215-5223 (1991).

Bellner, J. et al. Transcranial Doppler sonography pulsatility index (PI) reflects intracranial pressure (ICP). Surg Neurol 62, 45-51—discussion 51 (2004).

Binz, D. D., et al. Hemorrhagic complications of ventriculostomy placement: a meta-analysis. Neurocrit Care 10, 253-256 (2009).

Boas, D. A. et al. Haemoglobin oxygen saturation as a biomarker: the problem and a solution. Philos Transact A Math Phys Eng Sci 369, 4407-4424 (2011).

Boas, D. A. et al. Spatially varying dynamical properties of turbid media probed with diffusing temporal light correlation. JOSA A (1997).

Boas, D., et al. Scattering and Imaging with Diffusing Temporal Field Correlations. Phys Rev Lett 75, 1855-1858 (1995).

Böhmer, M., et al. "Time-resolved fluorescence correlation spectroscopy." Chemical Physics Letters 353.5-6 (2002): 439-445.

Bolognese, P., et al. Laser-Doppler flowmetry in neurosurgery. J Neurosurg Anesthesiol 5, 151-158 (1993).

Borycki, D., et al. "Interferometric Near-Infrared Spectroscopy (iNIRS) for determination of optical and dynamical properties of turbid media." Optics express 24.1 (2016): 329-354.

Buckley, E. M. et al. A Novel Combined Frequency-Domain Near-Infrared Spectroscopy and Diffuse Correlation Spectroscopy System. in BIOMED BM3A.17 (OSA, 2014). doi:10.1364/BIOMED.2014.BM3A.17.

Buckley, E. M. et al. Cerebral hemodynamics in preterm infants during positional intervention measured with diffuse correlation spectroscopy and transcranial Doppler ultrasound. Opt Express 17, 12571-12581 (2009).

Buckley, E. M. et al. Early postoperative changes in cerebral oxygen metabolism following neonatal cardiac surgery: effects of surgical duration. J Thorac Cardiovasc Surg 145, 196-203-205.e1—discussion 203-5 (2013).

Buckley, E. M. et al. Sodium bicarbonate causes dose-dependent increases in cerebral blood flow in infants and children with single-ventricle physiology. Pediatr Res (2013). doi:10.1038/pr.2013.25.

Buckley, E. M., et al. Diffuse correlation spectroscopy for measurement of cerebral blood flow: future prospects. Neurophoton 1, 011009-011009 (2014).

Budohoski, K. P. et al. What comes first? The dynamics of cerebral oxygenation and blood flow in response to changes in arterial pressure and intracranial pressure after head injury. Br J Anaesth 108, 89-99 (2011).

Buhre, W., et al. "Extrapolation to zero-flow pressure in cerebral arteries to estimate intracranial pressure." British Journal of anaesthesia 90.3 (2003): 291-295.

Burton, A. C. On the physical equilibrium of small blood vessels. Am J Physiol 164, 319-329 (1951).

(56) References Cited

OTHER PUBLICATIONS

Carp, S. A. et al. Due to intravascular multiple sequential scattering, Diffuse Correlation Spectroscopy of tissue primarily measures relative red blood cell motion within vessels. Biomed Opt Express 2, 2047-2054 (2011).
Carp, S. A., et al. Recovery of brain blood flow changes from diffuse correlation spectroscopy data using a layered Monte Carlo forward model. in Biomedical Optics 2014, OSA Technical Digest, Optical Society of America, 2014 (2014).
Carp, S. A., et al. Validation of diffuse correlation spectroscopy measurements of rodent cerebral blood flow with simultaneous arterial spin labeling MRI; towards MRI-optical continuous cerebral metabolic monitoring. Biomed Opt Express 1, 553-565 (2010).
Chapman, P. H., et al. The relationship between ventricular fluid pressure and body position in normal subjects and subjects with shunts: a telemetric study. Neurosurgery 26, 181-189 (1990).
Chen, J. J. et al. MRI measurement of the BOLD-specific flow-volume relationship during hypercapnia and hypocapnia in humans. Neuroimage 53, 383-391 (2010).
Cheung, C., et al. In vivo cerebrovascular measurement combining diffuse near-infrared absorption and correlation spectroscopies. Phys Med Biol 46, 2053-2065 (2001).
Chovanes, G. I. et al. The predominance of metabolic regulation of cerebral blood flow and the lack of 'Classic' autoregulation curves in the viable brain. Surg Neurol Int 3, 12 (2012).
Czosnyka, M. et al. Critical closing pressure in cerebrovascular circulation. J. Neurol. Neurosurg. Psychiatr. 66, 606-611 (1999).
Dagal, A. et al. Cerebral blood flow and the injured brain: how should we monitor and manipulate it? Current Opinion in Anaesthesiology 24, 131-137 (2011).
De Riva, N. et al. Transcranial Doppler pulsatility index: what it is and what it isn't. Neurocrit Care 17, 58-66 (2012).
Dehaes, M. et al. Cerebral oxygen metabolism in neonatal hypoxic ischemic encephalopathy during and after therapeutic hypothermia. J Cereb Blood Flow Metab 34, 87-94 (2014).
Dewey, R. C., et al. Experimental cerebral hemodynamics. Vasomotor tone, critical closing pressure, and vascular bed resistance. J Neurosurg 41, 597-606 (1974).
Dietsche, G. et al. Fiber-based multispeckle detection for time-resolved diffusing-wave spectroscopy: characterization and application to blood flow detection in deep tissue. Appl Opt 46, 8506-8514 (2007).
Diop, M., et al. Calibration of diffuse correlation spectroscopy with a time-resolved near-infrared technique to yield absolute cerebral blood flow measurements. Biomed Opt Express 2, 2068-2081 (2011).
Dong, J., et al. "Diffuse correlation spectroscopy with a fast Fourier transform-based software autocorrelator." Journal of biomedical optics 17.9 (2012): 097004.
Dong, L. et al. Noninvasive diffuse optical monitoring of head and neck tumor blood flow and oxygenation during radiation delivery. Biomed Opt Express 3, 259-272 (2012).
Durduran, T. et al. Diffuse correlation spectroscopy for non-invasive, micro-vascular cerebral blood flow measurement. Neuroimage (2013). doi:10.1016/j.neuroimage.2013.06.017.
Durduran, T. et al. Optical measurement of cerebral hemodynamics and oxygen metabolism in neonates with congenital heart defects. J Biomed Opt 15, 037004 (2010).
Durduran, T. et al. Transcranial optical monitoring of cerebrovascular hemodynamics in acute stroke patients. Opt Express 17, 3884-3902 (2009).
Durduran, T., et al. Diffuse optics for tissue monitoring and tomography. Rep Prog Phys 73, 076701 (2010).
Early, C. B., et al. Dynamic pressure-flow relationships of brain blood flow in the monkey. J Neurosurg 41, 590-596 (1974).
Edwards, A. D. et al. Cotside measurement of cerebral blood flow in ill newborn infants by near infrared spectroscopy. Lancet 2, 770-771 (1988).

Eggeling, C. et al. Data registration and selective single-molecule analysis using multi-parameter fluorescence detection. J. Biotechnol. 86, 163-180 (2001).
Eid, J. S., et al. Data acquisition card for fluctuation correlation spectroscopy allowing full access to the detected photon sequence. Rev Sci Instrum 71, 361 (2000).
Favilla, C. G. et al. Optical bedside monitoring of cerebral blood flow in acute ischemic stroke patients during head-of-bed manipulation. Stroke 45, 1269-1274 (2014).
Franceschini, M. A. et al. Near-infrared spiroximetry: noninvasive measurements of venous saturation in piglets and human subjects. J Appl Physiol 92, 372-384 (2002).
Roche-Labarbe, N. et al. Somatosensory evoked changes in cerebral oxygen consumption measured non-invasively in premature neonates. Neuroimage (2013). doi:10.1016/j.neuroimage.2013.01.035.
Roche-Labarbe, N., et al. Assessment of Infant Brain Development. (Wiley-VCH, 2011).
Rowney, D. A., et al. Cerebrovascular carbon dioxide reactivity in children anaesthetized with sevoflurane. Br J Anaesth 88, 357-361 (2002).
Selb, J. et al. Sensitivity of near-infrared spectroscopy and diffuse correlation spectroscopy to brain hemodynamics: simulations and experimental findings during hypercapnia. Neurophoton 1, (2014).
Selb, J., et al. Comparison of a layered slab and an atlas head model for Monte Carlo fitting of time-domain near-infrared spectroscopy data of the adult head. J Biomed Opt 19, 16010 (2014).
Selb, J., et al. Improved sensitivity to cerebral hemodynamics during brain activation with a time-gated optical system: analytical model and experimental validation. J Biomed Opt 10, 11013 (2005).
Selb, J., et al. Sensitivity of Continuous-Wave NIRS and Diffuse Correlation Spectroscopy to Cerebral Hemodynamics during Hypercapnia. in Biomedical Optics 2014, OSA Technical Digest, Optical Society of America, 2014 BT5B.6. (2014).
Selb, J., et al. Time-gated optical system for depth-resolved functional brain imaging. J Biomed Opt 11, 044008 (2006).
Shang, Y. et al. Cerebral monitoring during carotid endarterectomy using near-infrared diffuse optical spectroscopies and electroencephalogram. Phys Med Biol 56, 3015-3032 (2011).
Smith, M. Monitoring Intracranial Pressure in Traumatic Brain Injury. Anesth Analg 106, 240-248 (2008).
Stein, S. C., et al. Relationship of aggressive monitoring and treatment to improved outcomes in severe traumatic brain injury. J Neurosurg 112, 1105-1112 (2010).
Steiner, L. A. et al. Monitoring the injured brain: ICP and CBF. Br J Anaesth 97, 26-38 (2006).
Steiner, L. A. et al. Near-infrared spectroscopy can monitor dynamic cerebral autoregulation in adults. Neurocrit Care 10, 122-128 (2009).
Thees, C. et al. Relationship between intracranial pressure and critical closing pressure in patients with neurotrauma. Anesthesiology 96, 595-599 (2002).
Themelis, G. et al. Near-infrared spectroscopy measurement of the pulsatile component of cerebral blood flow and volume from arterial oscillations. J Biomed Opt 12, 014033 (2007).
Torricelli, A., et al. "Time domain functional NIRS imaging for human brain mapping." Neuroimage 85 (2014): 28-50.
Torricelli, A., et al. In vivo optical characterization of human tissues from 610 to 1010 nm by time-resolved reflectance spectroscopy. Phys Med Biol 46, 2227-2237 (2001).
Ursino, M. et al. A mathematical model of the relationship between cerebral blood volume and intracranial pressure changes: the generation of plateau waves. Ann Biomed Eng 19, 15-42 (1991).
Ursino, M. et al. A simple mathematical model of the interaction between intracranial pressure and cerebral hemodynamics. J Appl Physiol 82, 1256-1269 (1997).
Ursino, M., et al. Intracranial pressure dynamics in patients with acute brain damage: a critical analysis with the aid of a mathematical model. IEEE Trans Biomed Eng 42, 529-540 (1995).
Vajkoczy, P. et al. Continuous monitoring of regional cerebral blood flow: experimental and clinical validation of a novel thermal diffusion microprobe. J Neurosurg 93, 265-274 (2000).
Varsos, G. V. et al. Critical closing pressure determined with a model of cerebrovascular impedance. J Cereb Blood Flow Metab 33, 235-243 (2013).

(56) References Cited

OTHER PUBLICATIONS

Verdecchia, K, et al. "Quantifying the cerebral metabolic rate of oxygen by combining diffuse correlation spectroscopy and time-resolved near-infrared spectroscopy" Journal of biomedical optics 18.2 (2013): 027007.

Verdecchia, K.,et al. Multi-Distance Depth-Resolved Diffuse Correlation Spectroscopy. in Biomedical Optics 2014, OSA Technical Digest, Optical Society of America, 2014 (2014).

Wagner, B. P. et al. Dynamic cerebral autoregulatory response to blood pressure rise measured by near-infrared spectroscopy and intracranial pressure. Crit. Care Med 30, 2014 (2002).

Weerakkody, R. A. et al. Slow vasogenic fluctuations of intracranial pressure and cerebral near infrared spectroscopy—an observational study. Acta Neurochir 152, 1763-1769 (2010).

Williams, M. et al. Intraoperative blood pressure and cerebral perfusion: strategies to clarify hemodynamic goals. Paediatr Anaesth 24, 657-667 (2014).

Yodh, A. G., et al. "Pulsed diffusing-wave spectroscopy: High resolution through nonlinear optical gating." Physical review B 42.7 (1990): 4744.

Yu, G. et al. Validation of diffuse correlation spectroscopy for muscle blood flow with concurrent arterial spin labeled perfusion MRI. Opt Express 15, 1064-1075 (2007).

Yücel, M. A. et al. Validation of the hypercapnic calibrated fMRI method using DOT-fMRI fusion imaging. Neuroimage (2014). doi:10.1016/j.neuroimage.2014.08.052.

Yücel, M. A., et al. Reducing motion artifacts for long-term clinical NIRS monitoring using collodion-fixed prism-based optical fibers. Neuroimage 85 Pt 1, 192-201 (2014).

Zhou, C. et al. Diffuse optical monitoring of hemodynamic changes in piglet brain with closed head injury. J Biomed Opt 14, 034015 (2009).

Zirak, P. et al. Transcranial diffuse optical monitoring of microvascular cerebral hemodynamics after thrombolysis in ischemic stroke. J Biomed Opt 19, 18002 (2014).

Zirak, P., et al. Microvascular versus macrovascular cerebral vasomotor reactivity in patients with severe internal carotid artery stenosis or occlusion. Acad Radiol 21, 168-174 (2014).

Zuluaga, M. T., et al. "Diagnosis Influences Response of Cerebral NIRS to Intracranial Hypertension in Children." Pediatric critical care medicine: a journal of the Society of Critical Care Medicine and the World Federation of Pediatric Intensive and Critical Care Societies 11.4 (2010): 514.

Japan Patent Office. Notification of Reasons for Refusal for application 2017-552841. dated Aug. 25, 2020. With translation. 6 pages.

Japan Patent Office. Decision to grant patent for application 2017-552841. dated Jan. 12, 2021. With translation. 5 pages.

China National Intellectual Property Administration, Notice on the Second Office Action for application 201680032216.3. dated Jan. 25, 2021. With translation. 18 pages.

Japan Patent Office. Notification of Reasons for Refusal for application 2017-552842. dated Jan. 16, 2020. With translation. 8 pages.

Japan Patent Office. Decision to grant patent for application 2017-552842. dated Oct. 6, 2020. With translation. 5 pages.

Japan Patent Office. Notification of Reasons for Refusal for application 2017-552842. dated Jun. 2, 2020. With translation. 6 pages.

Sethaput, T.. Mathematical model for hemodynamic and intracranial Windkessel mechanism. Diss. Case Western Reserve University, 2013.

Fundamental Theorem of Calculus (http://mathmistakes.info/facts/CalculusFacts/Learn/doi/doi.html#:-text:=The%20conclusion%20of%20the%20fundamental%20theorem%20of%20calculus%20can%20be,undoes%20the%20result%20of%20integration%22.&text=so%20we%20see%20that%20the,)%20is%20f(x)., retrieved Oct. 18, 2020).

Witt, J-P et al. "Cerebral blood flow response pattern during balloon test occlusion of the internal carotid artery." American journal of neuroradiology 15.5 (1994): 847-856.

\* cited by examiner

SYSTEM AND METHOD FOR NON-INVASIVELY MONITORING INTRACRANIAL PRESSURE

CROSS-REFERENCE TO RELATED APPLICATIONS

This application is a U.S. National Phase of PCT Application No. PCT/US2016/026920 filed on Apr. 11, 2016 which is based on, claims the benefit of, and incorporates herein in its entirety, U.S. Provisional Patent Application Ser. No. 62/145,087 filed on Apr. 9, 2015, and entitled "SYSTEMS AND METHODS FOR MEASURING TISSUE PRESSURE."

BACKGROUND

The disclosure relates generally to systems and methods for measuring tissue properties using diffuse correlation spectroscopy (DCS). More particularly, the disclosure is directed to systems and methods for non-invasively measuring intracranial pressure, and other related parameters.

Unlike the other organs of the body, the tissue pressure of the brain is not coupled to atmospheric pressure. Instead, the brain experiences a unique intracranial pressure determined by the volume of brain tissue, cerebrospinal fluid, and intracerebral blood enclosed within a fixed volume confined by the rigid, non-expandable skull:

$$V_{Intercranial} = V_{tissue} + V_{CSF} + CBV. \quad (1)$$

Under normal circumstances, small increases in the volume of one of these components is compensated by reductions in the others to maintain intracranial pressure within normal ranges through a process known as spatial compensation. Spatial compensation is possible because, in the absence of injury or disease, cerebral spinal fluid freely flows between the cranial and spinal compartments and epidural venous blood is easily expelled from the spinal canal. Thus, some amounts of blood or cerebral spinal fluid can redistribute as necessary between cranial and extra-cranial regions of the dural sac. Furthermore, compensation of the total volume of cerebral spinal fluid can occur by alteration of the rate of cerebral spinal fluid absorption.

When spatial compensation is insufficient or compromised, the constituents of the cranio-spinal system have limited capacities for compression under pressure, leading to an intracranial volume that is actually partially elastic, rather than fully rigid:

$$V_{Intercranial} = V_{equilibrium} + V_{elastic} \quad (2)$$

where $V_{equilibrium}$ is the intracranial volume under normal intracranial pressure and $V_{elastic}$ is the change in volume of the craniospinal system due to changes exceeding accommodation by spatial compensation. In infants, deformation of the compliant immature skull allows further elasticity. Cerebral compliance, defined by $\Delta V/\Delta P$, represents the rigidity of the craniospinal compartment and is an indicator of the compensatory reserve for buffering changes in volume. Compliance is not constant but decreases with increasing pressure and can be impaired by pathology.

In pathological conditions such as traumatic brain injury (TBI), a cascade of events including brain swelling, vascular engorgement, obstruction of cerebrospinal fluid, edema, and/or intracranial hemorrhage, can exhaust compensatory mechanisms and lead to an exponential increase in intracranial pressure, as shown in FIG. 1. Compared to normal intracranial pressures typically around 10 mmHg, intracranial pressures in the range between 11-20 mmHg, 21-40 mmHg, and greater than 40 mmHg, representing slightly increased, moderately increased and severely increased values, respectively, pose an increasing risk for clinical complications. For instance, elevated intracranial pressures can dangerously reduce cerebral perfusion pressure and cerebral blood flow, causing ischemic brain injury (FIG. 2A). Since cerebral compliance decreases with increasing intracranial pressure, similar sized volume changes, including pulsatile blood volumes, result in larger changes in pressure. The risk is greatest when cerebral perfusion pressure is driven outside of the range of cerebral autoregulation, where cerebral blood flow is uncontrolled and passively follows pressure. Furthermore, the autoregulatory region can be reduced and shifted by both chronic and acute pathology (FIG. 2B). For example, in chronic hypertension or sleep apnea, vessels adapt to higher pressures or elevated $paCO_2$, shifting basal vessel tone, reducing the range of autoregulated cerebral vascular resistance, and raising the cerebral perfusion pressure ischemic limit.

Perfusion reserve is the difference between measured cerebral perfusion pressure and the lower pressure limit of autoregulation and is an important clinical indicator for assessing risk of ischemic injury. For example, in managing intracerebral hemorrhage, interventions lowering blood pressure may lead to undesirable ischemia, while maintaining blood pressure may lead to hyperemia and the risk of hematoma expansion. Determining perfusion reserve can help to maintain optimal cerebral blood flow, limiting risk and achieving better outcomes. Increased intracranial pressure can also cause serious injury or death through physical extrusion of brain tissue through rigid extra-cerebral features such as the dura mater tentorium or foramen magnum and/or compression of the brain stem. Decreased intracranial pressure can cause hemorrhage or even ventricle collapse, with greatest risk occurring during interventions such as cerebrospinal fluid drainage.

Because increased intracranial pressure is an important cause of secondary brain injury, and its degree and duration is associated with poorer outcomes, monitoring intracranial pressure is recommended for the management of a wide range of disorders. For example, these may include traumatic brain injury, intra-cerebral and subarachnoid hemorrhage, hydrocephalus, benign intracranial hypertension, cerebral edema, stroke, meningitis, central nervous system infections, acute liver failure, hepatic encephalopathy, and so forth. Continuous monitoring of intracranial pressure to guide the clinical management of patients is associated with significantly improved outcomes.

Since its first use in the 1950's, intracranial pressure has been measured invasively using an intracranial catheter inserted into the lateral ventricle, via a small hole burred through the skull, and connected to an external pressure transducer. This method is accurate and low-cost, and also accommodates therapeutic cerebrospinal fluid drainage and administration of drugs. However, it is an invasive procedure that can be associated with complications, including hemorrhage and infection. Moreover, in some situations, such as patients having idiopathic intracranial hypertension, anticoagulation, sepsis, liver disease, or aerospace travel in microgravity environments, this invasive procedure is not appropriate.

Development of non-invasive monitoring of intracranial pressure is recognized as an urgent need to avoid the complications of invasive procedures and to extend diagnostics to patients whose risk may be substantial but not enough to justify an invasive procedure. In addition, noninvasive intracranial pressure measurements could be used to identify patients needing invasive procedures, as well as to provide important information in the critical periods. In some applications, a combination of non-invasive and invasive intracranial pressure monitoring could also be beneficial. This is because often the reliability of invasive monitors is impaired for structural reasons, such as the presence of a ventricular drain, or due to artifacts like sensor fouling. As such, redundant non-invasive sensors would be a valuable adjunct. A non-invasive monitor of ICP and related cerebral measures, such as cerebral vascular resistance, cerebral perfusion pressure, vessel wall tone, cerebral blood flow-cerebral spinal fluid pulsatility coupling and cerebral compliance, dynamic autoregulation, cerebral perfusion reserve, and others, would also create many new applications in areas where invasive monitoring is not appropriate.

As a result, significant research efforts have been aimed towards the development of noninvasive methods to measure intracranial pressure using transcranial Doppler ultrasonography, tympanic membrane displacement, optic nerve sheath diameter, fundoscopy, computed tomography and magnetic resonance imaging. However, none of these techniques can be performed continuously at the bedside, and none have yet achieved the accuracy required to become routine clinical practice.

One widely used approach for estimating ICP has included determining a pulsatility index using transcranial Doppler ultrasonography measurements. The principle behind it is that the pulsatility of blood flow velocity through cerebral arterial vessels reflects distal cerebrovascular resistance, and hence intracranial pressure. As such, many have suggested utilizing the pulsatility index to estimate the intracranial pressure and cerebral perfusion pressure. However, the pulsatility index is not dependent solely on cerebrovascular resistance, but is dependent on the interplay between cerebral perfusion pressure, pulse amplitude of arterial blood pressure, cerebrovascular resistance, compliance of the cerebral arteries and heart rate. As such, the pulsatility index is not an accurate estimator of intracranial pressure due to the confounding contributions.

Also, the accuracy of the pulsatility index determined using transcranial Doppler ultrasonography also strongly depends on ultrasound probe position and uniform insonation of the middle cerebral artery. In addition, in approximately 10-15% of patients, ultrasound cannot penetrate the skull. In these cases, transcranial Doppler ultrasonography cannot provide usable measurements. Furthermore, transcranial Doppler ultrasonography cannot be used as a continuous monitor because of the rigid and bulky transducer utilized.

Near-infrared spectroscopy, on the other hand, can monitor regional cerebral blood volume and hemoglobin oxygenation ($SO_2$) continuously at the bedside. As a result, near-infrared spectroscopy has been used to estimate cerebrovascular reactivity indices, which correlate with intracranial pressure. However, these measurements are not sufficiently independent from other hemodynamic parameters to provide accurate measures of intracranial pressure.

Consequently, considering the limitations of previous technological approaches, systems and methods capable of non-invasively and accurately measuring intracranial pressure, due to pathological and other medical conditions, are highly desirable.

SUMMARY

The present disclosure overcomes the aforementioned drawbacks by providing a system and method for accurately and non-invasively monitoring patients. More specifically, the system and method described herein utilizes diffuse correlation spectroscopy to measure pulsatile, as well as steady, cerebral blood flow for determining parameters useful in the diagnosis and management of patients. In particular, the system and method provided herein can be used to measure intracranial pressure, and other parameters, such as cerebral perfusion pressure, vessel wall tone, cerebral blood flow-cerebral spinal fluid pulsatility coupling and cerebral compliance, dynamic autoregulation, and cerebral perfusion reserve.

As will be described, the present approach may not only provide valuable information, on a continuous basis, for administering acute care at a patient bedside or in an ambulance, but also provide information for analyzing complex pathophysiology, identifying new therapeutic opportunities, and, in general, substantially improving neurocritical care management. In some applications, the present approach may be used in the diagnosis, monitoring and treatment of traumatic brain injury or concussions, as well as other brain conditions.

In one aspect of the disclosure, a system is provided for non-invasively monitoring intracranial pressure. The system includes an optical coupling system configured to transmit and receive light signals from one or more locations about a subject and an optical processing system configured to generate diffuse correlation spectroscopy (DCS) data at a temporal resolution greater than a pulsatile frequency of cerebral blood flow of the subject using the transmitted and received light signals. The system also includes a computer programmed to receive the DCS data, analyze the DCS data to determine a pulsatile cerebral blood flow, and correlate the determined pulsatile cerebral blood flow with physiological data acquired from the subject. The computer is also programmed to estimate an intracranial pressure based on the correlation and generate a report indicative of the estimated intracranial pressure.

In another aspect of the disclosure, a method for non-invasively estimating intracranial pressure is provided. The method includes acquiring diffuse correlation spectroscopy (DCS) data at a temporal resolution greater than a pulsatile frequency of cerebral blood flow of a subject using one or more optical sensors placed about the subject, and determining a pulsatile cerebral blood flow using the acquired data. The method also includes correlating the determined pulsatile cerebral blood flow with physiological data acquired from the subject, and estimating an intracranial pressure based on the correlation. The method further includes generating a report indicative of the estimated intracranial pressure.

In yet another aspect of the disclosure, a method for non-invasively monitoring a subject using a monitoring system is provided. The method includes acquiring diffuse correlation spectroscopy (DCS) data at a temporal resolution greater than a pulsatile frequency of cerebral blood flow of a subject using one or more optical sensors placed about the subject, and determining a pulsatile cerebral blood flow using the acquired data. The method also includes correlating the determined pulsatile cerebral blood flow with physiological data acquired from the subject using physiological sensors, and estimating at least one parameter based on the correlation. The method further includes generating a report indicative of the at least one parameter estimated.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

The brain is enclosed in a rigid skull, and as a result, changes in intracranial pressure (ICP) affect cerebral blood flow (CBF), which can lead to serious medical conditions, such as cerebral ischemia. Therefore, intracranial pressure (ICP) monitoring is highly desirable for the diagnosis and treatment of patients with a wide range of medical conditions and disorders, including traumatic brain injury, intracerebral and subarachnoid hemorrhage, hydrocephalus, benign intracranial hypertension, meningitis, stroke, acute liver failure, and so forth.

Therefore, in accordance with aspects of the present disclosure, a system and a method for accurate, non-invasive monitoring of ICP based on diffuse correlation spectroscopy (DCS), are described herein. In particular, the system and method can measure CBF and more specifically pulsatile cerebral blood flow (pCBF) to determine ICP, as well as other clinically relevant parameters, such as cerebral perfusion pressure (CPP), cerebrovascular resistance (CVR), vessel wall tone, cerebral blood flow-cerebral spinal fluid pulsatility coupling and cerebral compliance, dynamic autoregulation, cerebral perfusion reserve, and other parameters. This approach recognizes that the pressure-axis intercept in the pulsatile pressure-flow relationship curve (FIG. 3), namely the critical closing or zero flow pressure (CrCP), is directly related to ICP.

Figure 1:
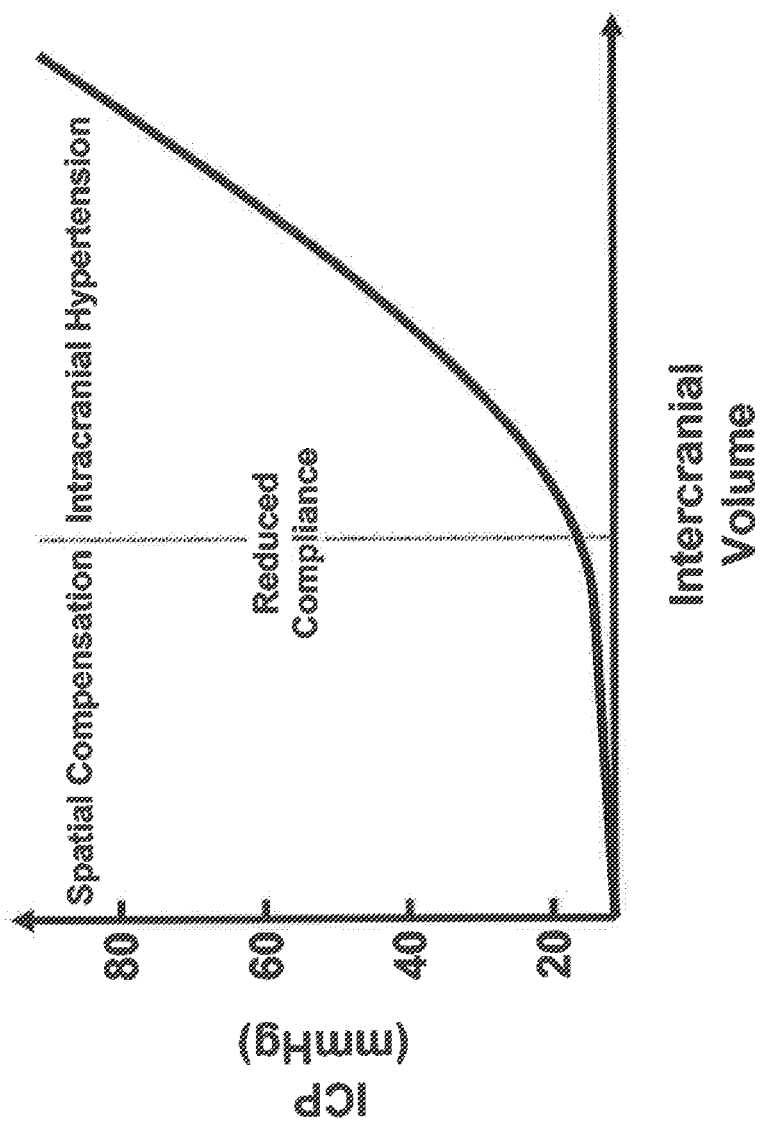
FIG. 1 is a graph showing a relationship between intracranial volume and pressure.
Figure 2B:
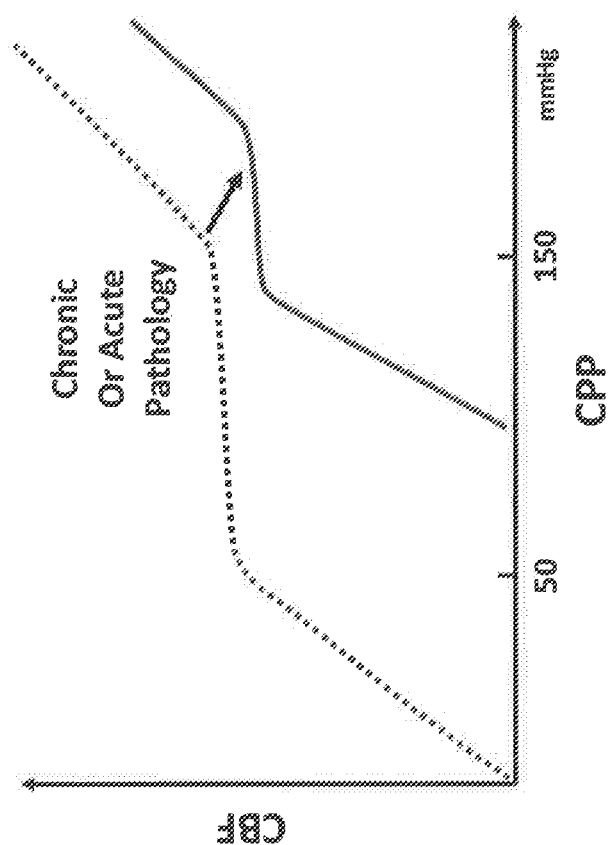
FIG. 2B is a graph showing changes in the optimal perfusion due to certain medical conditions.
Figure 2A:
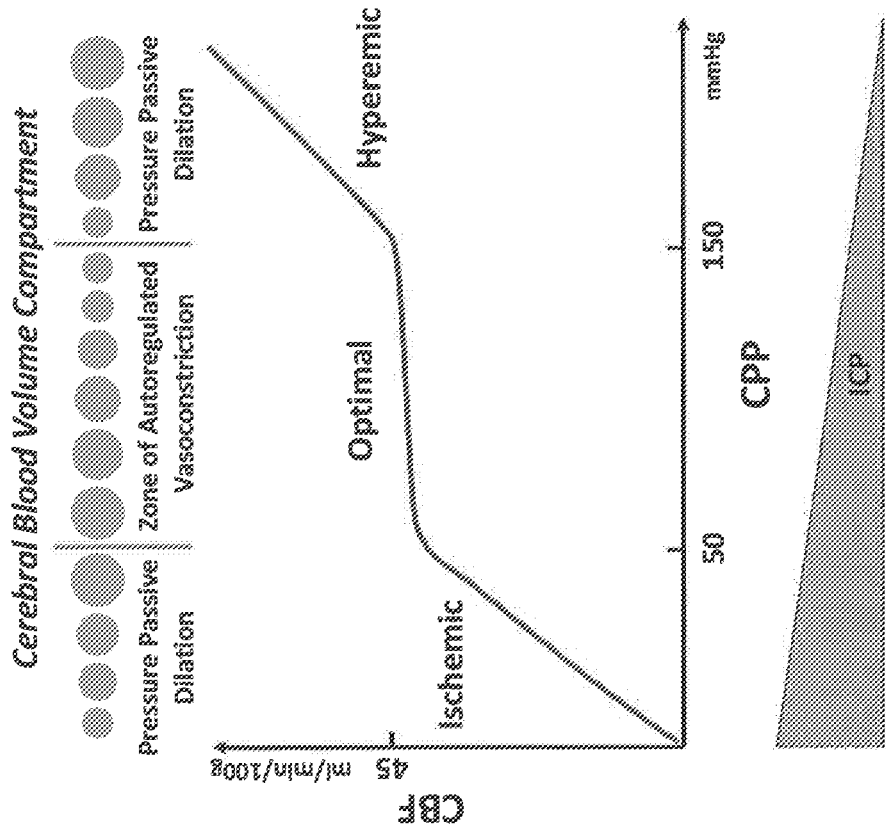
FIG. 2A is a graphical illustration showing clinical zones of cerebral perfusion relative to intracranial pressure.
Figure 3:
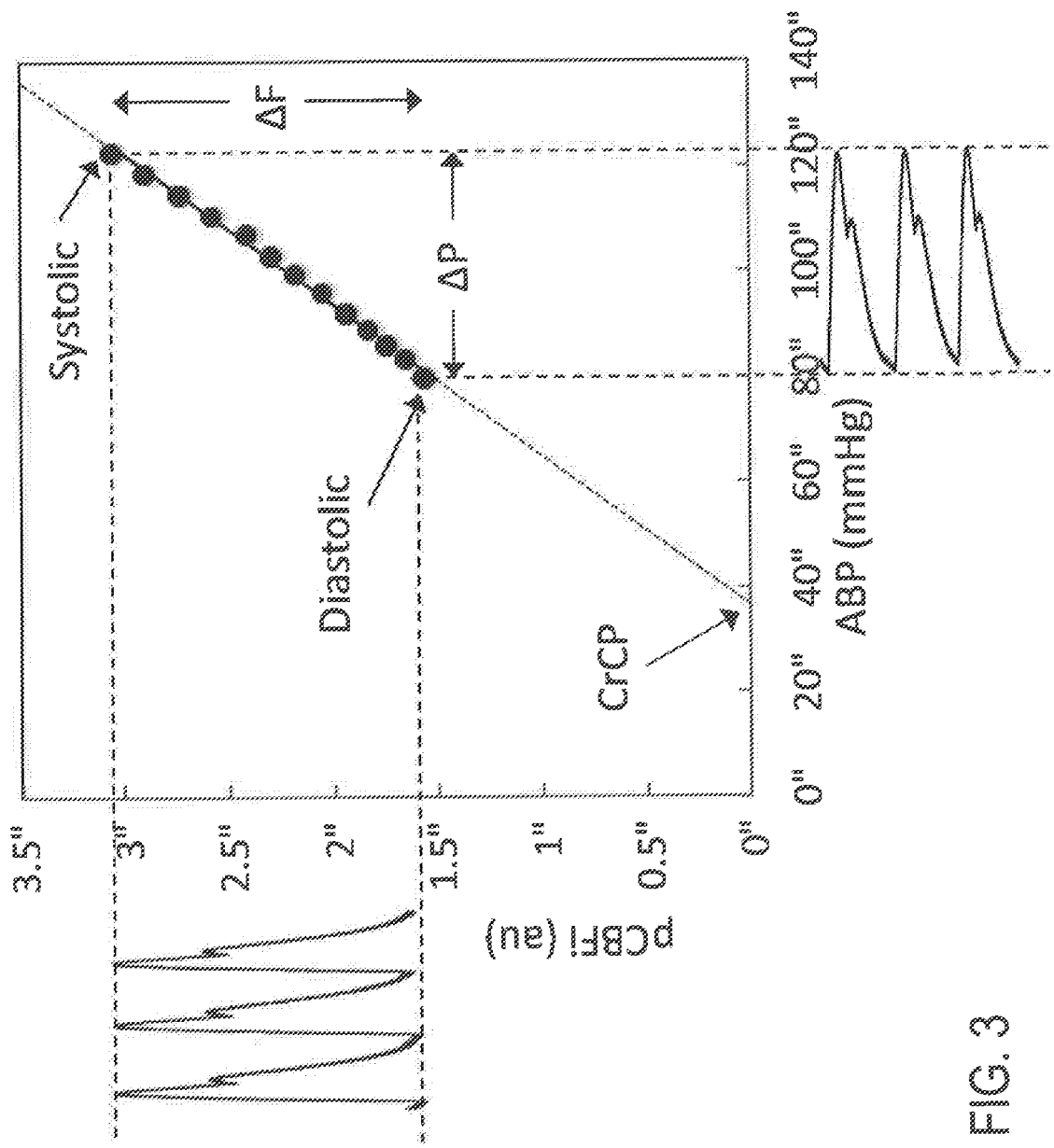
FIG. 3 is a graph illustrating the relationship between pulsatile blood flow and arterial blood pressure.

In particular, FIG. 3 is a graph showing an index of pulsatile cerebral blood flow (pCBFi) from cerebral vessels versus arterial blood pressure (ABP). As labeled, this graph shows that CrCP is present at zero pCBFi and that the pulsatility of blood from the diastolic to systolic results in a corresponding variation in pressure ($\Delta P$) and variation in flow ($\Delta F$). As will be described, the system and method of the present disclosure are able to acquire DCS data at a speed, or temporal resolution sufficient to determine pCBF and use pCBF and other measures to non-invasively determine clinically-useful information with an accuracy and precision that has not previously been available using non-invasive systems. For example, as will be described, the system and method of the present disclosure are capable of acquiring and processing multiple DCS measurements per second to, thereby, achieve a speed, or temporal resolution, to determine pulsatile information and create accurate measures not achieved or recognized in non-invasive systems previously. This stands in contrast to traditional DCS systems and methods that, for example, have a sampling time for DCS measurements of approximately 1.5 seconds or longer.

Also, the present approach can be used for non-invasive continuous monitoring over extended periods of time with minimized interference or discomfort to a patient. As such, the provided system and method may be suitable for continuous or discrete measurements in a much larger population including adults, children, infants, neonates, and premature infants. This includes patients not undergoing invasive procedures or those for whom an invasive procedure might not be worth the risk. In addition, using the system and method described, measurements can be made on patients while conscious or unconscious, awake or sedated or anesthetized. In addition to humans, the provided system and method may be used with animals for research, commercial, and/or veterinary purposes. Furthermore, the present approach may also be used to measure perfusion pressure of other organs besides the brain.

Previous non-invasive techniques, such as near-infrared spectroscopy and transcranial Doppler ultrasonography, measure blood volume or blood flow velocity measurements, respectively, to estimate ICP. As described, these approaches rely on surrogate measurements, and include a variety of confounding factors that prevent accurate determination of ICP. For example, transcranial Doppler ultrasonography utilizes the middle cerebral artery, which averages the blood supply of many anatomically distinct regions, including those with less sensitivity to ICP. Accordingly, these systems are not able to accurately assess pulsatility and, thereby, are not able to provide accurate determinations of ICP.

By contrast, the present approach utilizes DCS to measure blood flow directly. In particular, DCS can be used to measure CBF in cortical microvessels, which have lower tension and are more sensitive to cranial pressure changes compared with larger arteries. Also, DCS can be used to measure CBF specifically within brain tissue, and overcome confounding factors of middle cerebral artery measurements. Furthermore, DCS provides a robust average of CBF over $cm^3$-sized cortical volumes, without being sensitive to probe placement or orientation, as transcranial Doppler ultrasonography. Thus, the systems and methods are able to perform absolute calibration of blood flow, unlike other non-invasive systems and methods.

Figure 4B:
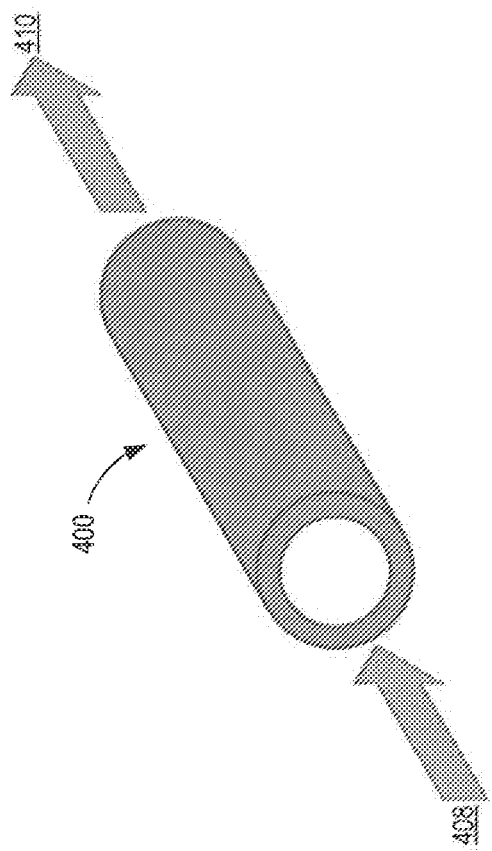
FIG. 4B is an illustration showing perfusion pressure along a blood vessel.
Figure 4A:
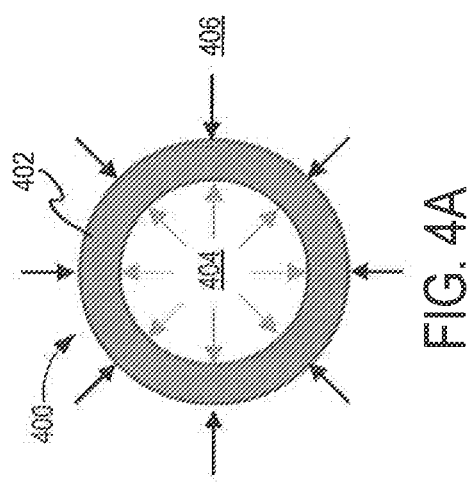
FIG. 4A is an illustration showing transmural pressure across a blood vessel wall.

Primarily, two types of pressures act upon the cerebral vasculature to influence blood flow, namely transmural pressure and perfusion pressure, as illustrated in FIGS. 4A and 4B. Referring particularly to FIG. 4A, transmural pressure is the net pressure acting across the wall 402 of a blood vessel 400 resulting from an internal hydrostatic transmural pressure 404 and an external hydrostatic transmural pressure 406. Specifically, the internal hydrostatic transmural pressure 404 is an outward pressure as a result of blood pressure. On the other hand, in the skull, the external hydrostatic transmural pressure 406 is primarily the intracranial pressure.

Classically, transmural pressure gives rise to Starling forces and drives transudate and exudate transport through blood vessel walls throughout the organs of the body. Transmural pressure is less associated with tissue blood perfusion. However, within the rigid confines of the skull, ICP-dominated transmural pressure can couple to the flow of blood through vessels via the elasticity of the vessels themselves.

Figure 5:
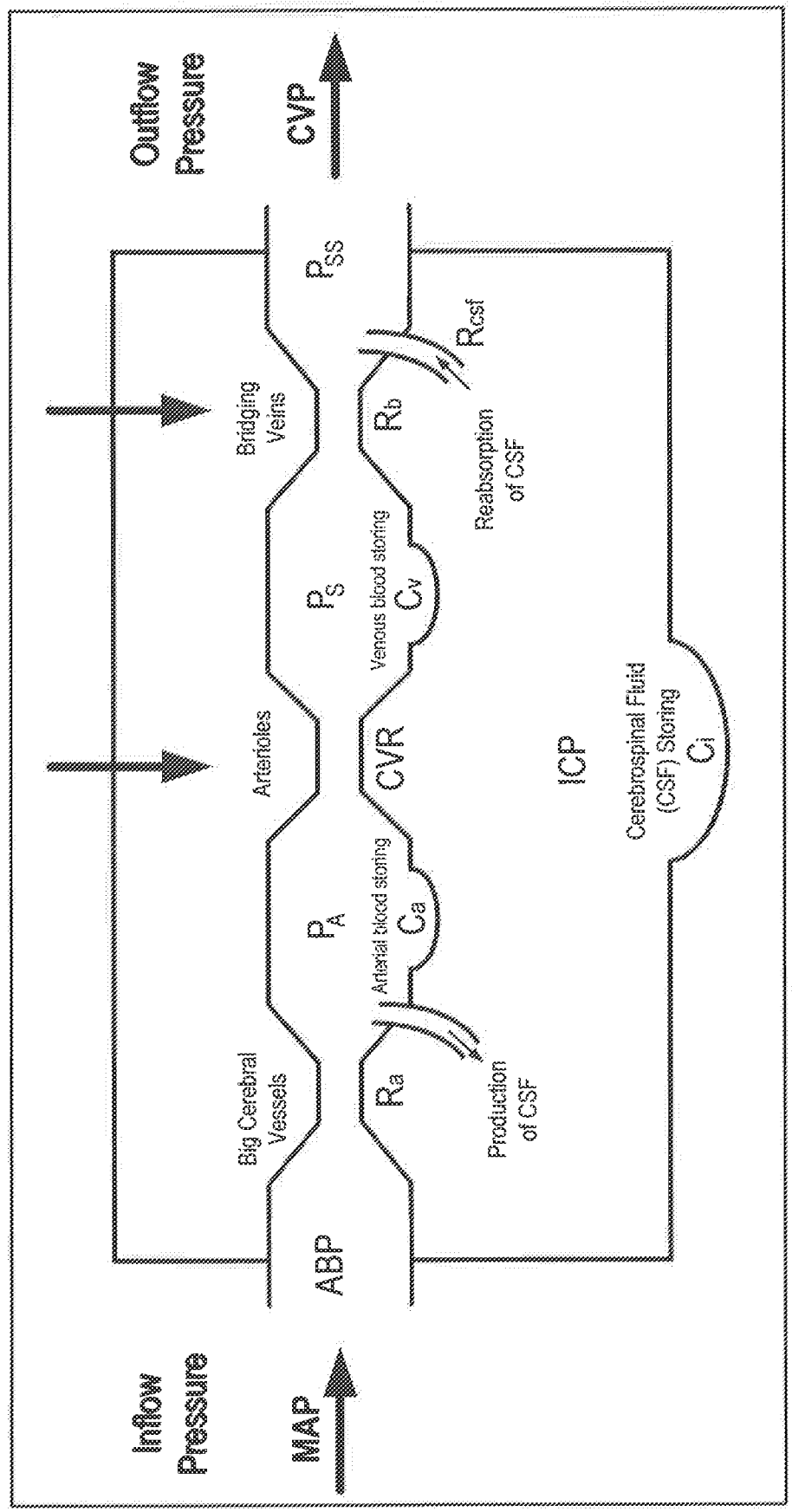
FIG. 5 is a schematic diagram of a model indicating vascular elements affecting cerebral perfusion.

When the transmural pressure is great enough to compress the flexible vessels, their internal diameters effectively decrease, and flow is impeded through the well-known Starling resistor phenomenon (FIG. 5). In the extreme, when transmural pressure becomes negative, the vessel will collapse and close entirely to flow. For example, externally generated negative transmural pressures are the basis for well-known sphygmomanometer measurements of blood pressure.

Perfusion pressure, on the other hand, is directly related to tissue perfusion and is defined as the difference in pressure between the vascular inflow and outflow within the vessel or vascular network. Referring specifically to FIG. 4B, the perfusion pressure across the blood vessel 400 is the difference between the inflow pressure 408 and outflow pressure 410. Furthermore, perfusion pressure is related to blood flow through the vascular resistance in a relationship with blood flow that is similar to Ohm's law. Under normal circumstances, vascular resistance is regulated under physiological control, including functional hyperemia, in response to $PaCO_2$ levels, and autoregulation. Pharmacological agents, injury and disease can also impact vascular resistance and its physiological control mechanisms.

Figure 4C:
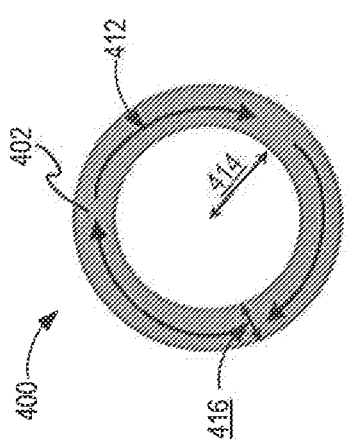
FIG. 4C is an illustration showing tension around a blood vessel wall.

The properties of blood vessels affect blood flow therethrough. Referring specifically to FIG. 4C, the wall tension 412 of a blood vessel 400 is shown a circumferential force within the wall 402. Wall tension 412 is related to the transmural pressure and the ratio of the internal radius 414 to the thickness 416 of the blood vessel 400. The wall tension 412 must be overcome for the blood vessel 400 to close. For vessels with the ability to actively dilate and contract, the vessel diameter is under physiological control. Thus, the wall tension 412 is also referred to as vessel tone.

Since the cerebral vasculature is enclosed by the rigid confines of the skull, ICP applies a transmural pressure external to the blood vessels, as shown in the diagram of FIG. 5. Under normal conditions, the outflow pressure is dominated by central venous pressure (CVP) and the transmural ICP has little effect on CPP. However, when ICP exceeds CVP, the transmural pressure acts to constrict the vessels at flexible sites, such as bridging vessels on the surface of the brain and arterioles, as indicated by the arrows shown in FIG. 5. In this case, these sites act as Starling resistors, restricting flow and reducing CPP. Under these conditions, the zero flow pressure quantifies the magnitude of ICP.

Conceptually, perfusion pressure is both a direct measure of the adequacy of tissue perfusion and, via the limits of autoregulation, an estimate of the amount of perfusion reserve available to maintain homeostasis. However, in practice, CPP is a quantity inferred from other measurements since it is typically not practical to measure outflow pressure directly. Thus, quantities such as ICP have been preferred for clinical use, although their relationship to pathology, namely the risk of ischemia, is indirect.

Measurements of CPP and CBF both provide information on the amount of tissue perfusion and the risk of ischemia. However, CBF can vary physiologically over two fold without injury. For example, if cerebral vessels dilate, CBF will increase. At the same time, cerebral vascular resistance would decrease correspondingly. In the relationship for CPP, under physiological conditions these two factors will tend to cancel, leaving CPP relatively unchanged. Thus, CPP may have greater sensitivity to pathological conditions with less influence from normal physiological variations. Furthermore, CPP and CBF can be combined with other measures, such as oxygen saturation ($SO_2$), oxygen extraction fraction (OEF), cerebral blood volume (CBV), cerebral metabolic rate of oxygen ($CMRO_2$) to further quantify ischemic risk and perfusion reserve.

Under normal conditions, cerebral perfusion pressure can be approximated as the difference between arterial pressure and central venous pressure. However, when ICP is sufficiently elevated, vascular resistance becomes dominated by Starling resistor effects and the effective outflow pressure is no longer CVP but ICP. Thus, ICP couples to CBF and measurements of CBF, either alone or in conjunction with other physiological measurements, can be used to determine ICP, risk of ischemia, loss of autoregulation and/or regulatory reserve, and/or other parameters.

Figure 6:
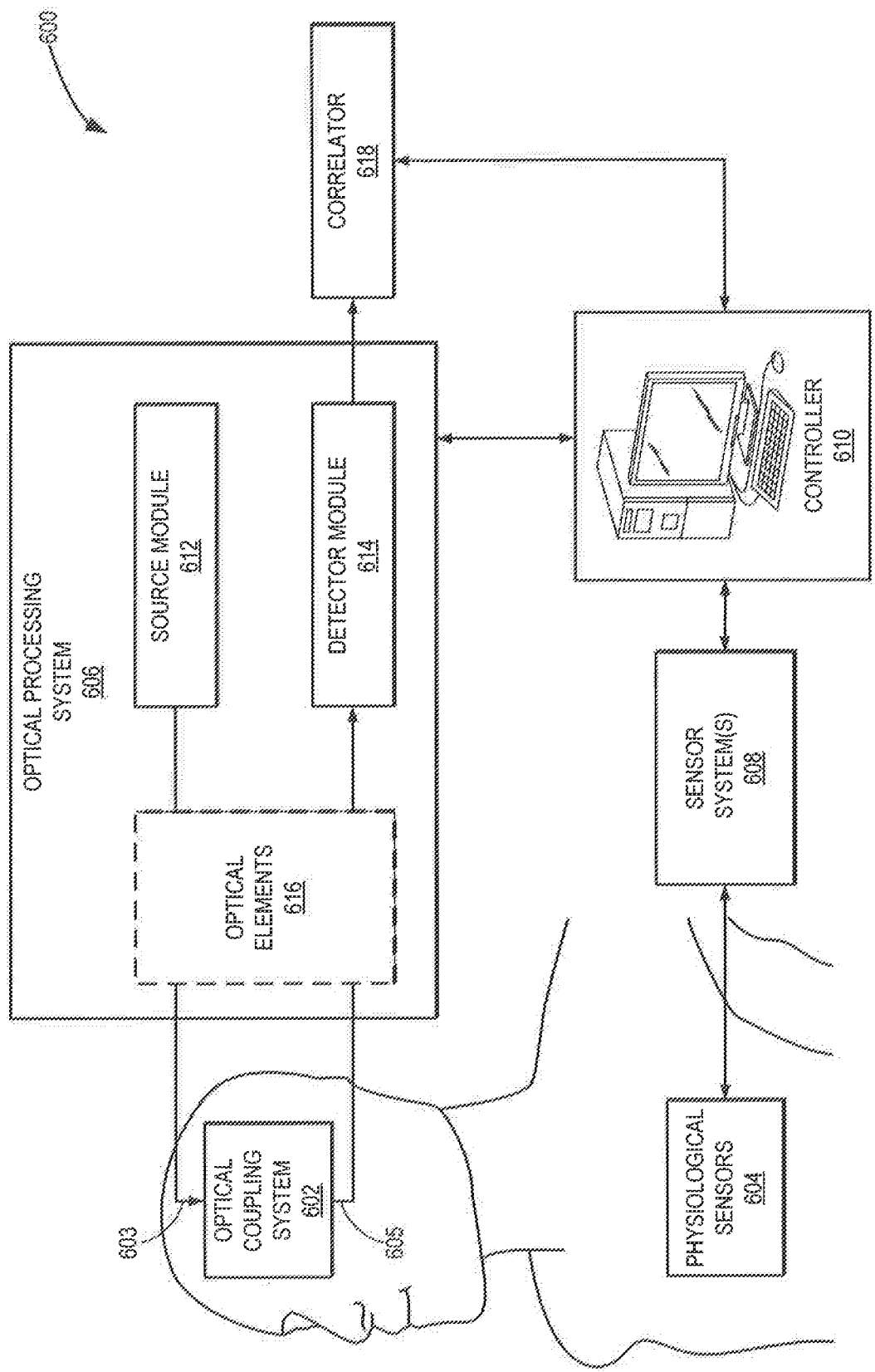
FIG. 6 is a diagram of an example monitoring system, in accordance with aspects of the present disclosure.

Turning to FIG. 6, a block diagram is shown of an exemplary system 600 for non-invasive monitoring of a subject, in accordance with aspects of the present disclosure. As shown, the system 600 generally includes a number of sensors, including an optical coupling system 602 and physiological sensors 604, to be placed at various locations about a subject's body. The system 600 also includes an optical processing system 606 and one or more sensor system(s) 608 in communication with the physiological sensors 604. The optical processing system 606 and sensor system(s) 608 are in communication with a controller 610 that is configured control operation of the system 600, and systems therein, including data acquisition and processing.

The system 600 may operate autonomously or semi-autonomously, or in conjunction with other devices or hardware. The system 600 may also read executable software instructions from a non-transitory computer-readable medium (such as a hard drive, a CD-ROM, flash memory and the like), and may also receive instructions from a user, or any other source logically connected thereto, such as another networked computer or server, database, internet, cloud, and so forth.

The optical coupling system 602 may include a number of source probes 603 and detector probes 605 forming one or more optical sensors, including DCS sensors, and near infra-red spectroscopy (NIRS) sensors. In particular, the source probes 603 are configured to transmit light signals to the subject, while the detector probes 605 are configured to receive light signals therefrom. The source probes 603 and detector probes 605 can include single-mode and/or multimode optical fibers. The optical fibers may be straight fibers, 90° bent fibers, or side-firing fibers. The source probes 603 and detector probes 605 may be arranged in various configurations and separated by distances up to several centimeters. In some implementations, the optical coupling system 602 is configured for measuring blood flow in the brain, and optionally, blood flow in the skin, scalp, skull, and/or periphery.

The physiological sensors 604, controlled by the sensor systems(s) 608, may include electroencephalogram (EEG), electrocardiograph (ECG), blood pressure (BP), ICP, pulse oximetry, and other sensors, configured to measure physiological parameters, including, but not limited to, hemoglobin concentrations, changes in hemoglobin concentrations, oxygen saturation, $CMRO_2$, invasive blood pressure, non-invasive blood pressure, intracranial pressure, brain activity, electrocardiogram, cardiac output, stroke volume, and combinations thereof. In some implementations, physiological sensors 604 and respective sensor system(s) 608 may be from a separate device from a different manufacturer.

Various sensors described with reference to the optical coupling system 602 and physiological sensors 604 may be incorporated into, or be part of, one or more items or units designed to engage with or couple to a subject at any number of locations, in any number of geometrical configurations. For example, various sensors may be integrated into silicone assemblies, bandages, headbands, and any other assemblies securable to the subject. Also, various sensors may be wearable or designed to attach to the subject directly using an adhesive.

Although FIG. 6 shows the optical coupling system 602 placed about a subject's head, and physiological sensors 604 placed about the subject's torso, it may be readily appreciated that the locations of the sensors can vary, in accordance with the signals being induced and sensed. For example, various physiological sensors 604 may be placed about the subject's head, arms, legs, and so forth. Similarly, optical sensors may be placed about the subject's arms, legs, torso, and so forth. As such, different sensors may be collocated, or individually placed at various positions about the subject.

The optical processing system 606 is in communication with the optical coupling system 602 includes a source module 612 configured to generate light using one or more light sources. The source module 612 may be configured to operate in the continuous wave, frequency domain, and time domain. To this end, the source module 612 may be pulsed, sinusoidally modulated, step modulated, triangularly modulated, and/or arbitrarily modulated.

By way of example, the source module 612 may include a transform, or nearly-transform, limited picosecond pulsed source or a non-transform limited picoseconds pulsed source. As used herein, reference to "picosecond" pulses or pulsed source refers to pulses having a pulse width between 1 ps and 10 ns. The source module 612 may also include a Bragg reflector laser, a distributed Bragg feedback laser, a gain-switched distributed Bragg reflector laser, an external cavity laser, a gain-switched laser, a current pulsed laser, a mode-locked laser, a q-switched laser, combinations thereof, and the like. The source module 612 can also include a diode laser, a solid-state laser, a fiber laser, a vertical cavity surface-emitting laser (VCSEL), a Fabry-Perot laser, a ridge laser, a ridge waveguide laser, a tapered laser, a master oscillator power amplifier (MOPA) laser, or other type of laser. In certain aspects, the source module 612 can also include a swept source light source.

The source module 612 can be configured to transmit light into a target medium using wavelengths between 400 nm and 1500 nm, including but not limited to, a wavelength of between 600 nm and 1000 nm, or a wavelength of between 690 nm and 900 nm. The source module 612 can also be configured to transmit light into the target medium using average power between 10 μW and 10 W, including but not limited to, an average power of between 100 μW and 1 W, between 1 mW and 500 mW, or between 10 mW and 200 mW. The source module 612 can be configured to transmit light pulses into a target medium using pulse widths between 1 ps and 10 ns, including but not limited to, a pulse width of between 10 ps and 1 ns, or between 50 ps and 500 ps. Pulse widths described herein refer to full-width at half maximum pulse widths.

The optical processing system 606 also includes a detector module 614 in communication with the optical coupling system 602 which is configured to receive light signals from the subject and provide an output to a correlator 618 indicative of the received signals. For example, the detector module 614 may include one or more photon-counting avalanche photodiodes (APDs) configured to provide photon counts based on detected light. As shown in FIG. 6, the optical processing system 606 may optionally include a number of optical elements 616 interposed between the optical coupling system 602, source module 612 and detector module 614. Specifically, the optical elements 616 may be configured for manipulating light signals transmitted to and received from the subject. Example optical elements 616 include lenses, prisms, holograms or diffractive optical elements, diffusers, attenuators, filters, optical fibers, and so forth.

In general, the controller 610 may be a computer, as shown in FIG. 6, that is programmed to carry out steps in accordance with aspects of the present disclosure, as will be described. The controller 610 may also be a workstation, a laptop, a mobile device, a tablet, a personal digital assistant (PDA), a multimedia device, a network server, a mainframe or any other general-purpose or application-specific computing device. Other examples for the controller 610 may also include system on a chip (SOC) a field-programmable gate array (FPGA), a complex programmable logic device (CPLD), an application-specific integrated circuit (ASIC), a Raspberry PI controller, and the like.

In some aspects, the controller 610 may be configured to acquire and process optical, physiological and other signals induced or generated by a subject, to estimate desired physiological parameters. Specifically, the controller 610 may be configured to receive and utilize DCS measurements to determine a pulsatile, as well as steady, cerebral blood flow from which a number of physiological parameters, including ICP, CPP, CRV, and so forth, may be estimated. In some aspects, the controller 610 may utilize characteristics of a pulsatile pressure-flow relationship curve, as described with reference to FIG. 3 to determine desired physiological parameters. For example, the critical closing or zero flow pressure (CrCP), or intercept may be used to is directly related to ICP. Additionally, a slope of the pulsatile pressure-flow relationship may also be utilized by the controller 610, as well as any other information obtained therefrom.

Figure 7:
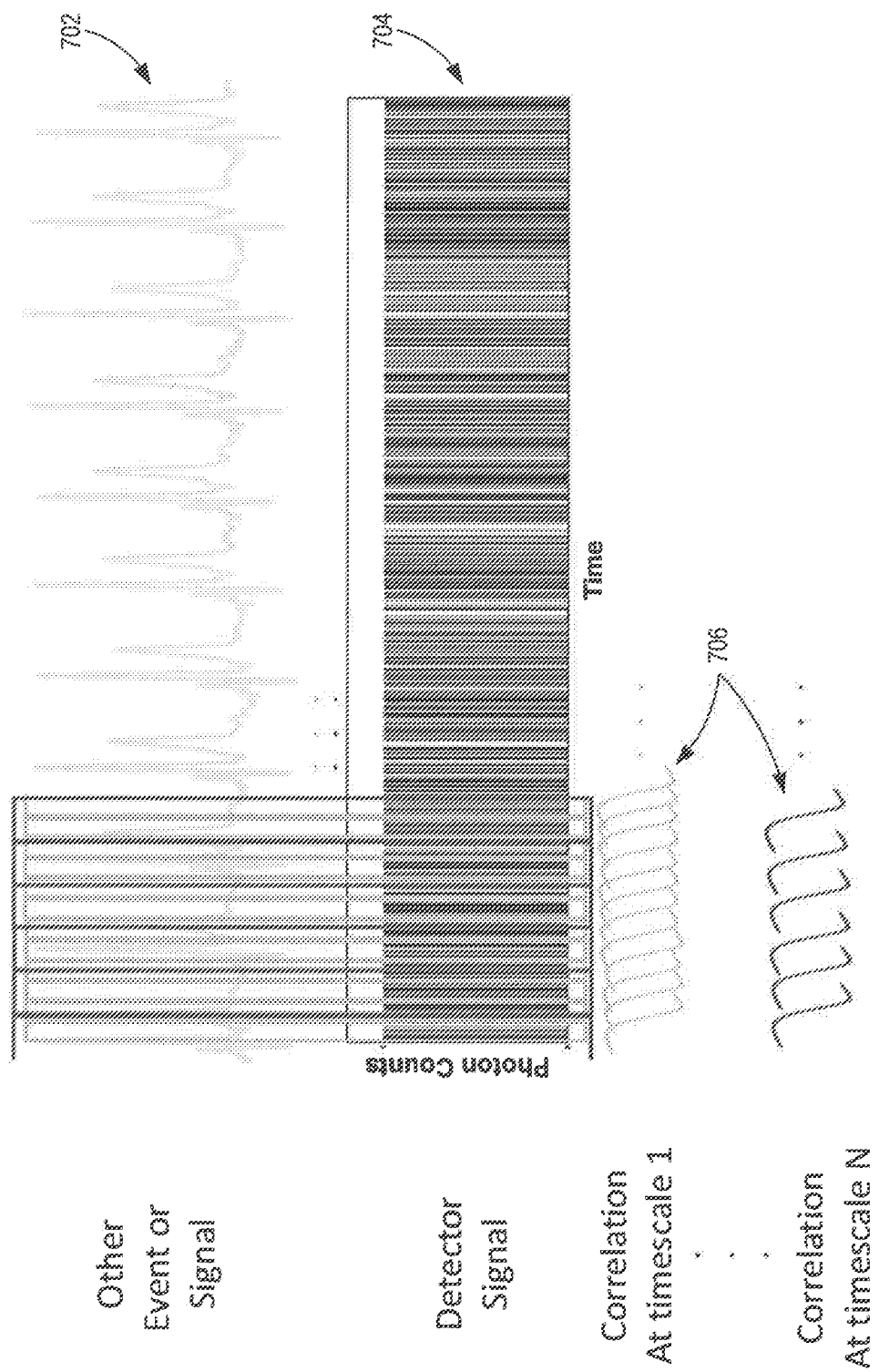
FIG. 7 is a graphical illustration showing acquisition, gating and averaging of photon count data, in accordance with aspects of the present disclosure.

In some aspects, the controller 610 may be configured to acquire simultaneous or synchronous measurements, as well as separate measurements, using various sensors placed on the subject, as described. Also, measurements may be made once, intermittently, periodic, continual, or continuously. The controller 610 may be configured to utilize signals from such measurements to construct various time series waveforms. For example, FIG. 7 shows acquisition of ECG data 702 and DCS data 704 as a function of time. The controller 610 may also be configured to assemble acquired signals into a frequency representation, as power spectra. As such, the controller 610 may be configured to apply a Fast Fourier Transform (FFT), for example, to the acquired signals. Other signal representations may also be generated by the controller 610, including signal derivatives, differentials, differences, and so forth. The controller 610 may also determine signal amplitudes, timing, phases, correlations, and so forth. Processing of signals by the controller 610 may be performed in real-time, near real-time, or by post-processing, either in the time or frequency domain or both.

In some aspects, the controller 610 of FIG. 6 may be configured to generate, by way of the correlator 618, correlation curves using acquired DCS data. In this manner, various desirable parameters, such as blood flow, and more specifically pulsatile blood flow, and others may be determined, as will be described. In particular, the correlator 618 may receive photon count data from the detector module 614 and calculate intensity autocorrelation functions at various time scales using the photon count data. Although the correlator 618 is shown in FIG. 6 as separate from the controller 610, it may be readily appreciated that these could be integrated into one system. For instance, the controller 610 may include various hardware and software for directly calculating intensity autocorrelation functions.

Referring again to FIG. 7, correlation curves 704, obtained at different time scales using DCS data, are shown. Such correlation curves may be generated either synchronously or asynchronously along with other acquired measurements, such as ECG and other physiological measurements. For example, DCS measurements may be collected at multiple times relative to the cardiac cycle measured using ECG data.

In some aspects, the optical processing system 606 in cooperation with the controller 610, and methods of operation of the present disclosure are capable of acquiring and processing multiple DCS measurements per second to, thereby, achieve a speed, or temporal resolution, to determine pulsatile information and create accurate measures not achieved or recognized in non-invasive systems previously. By way of example, data, including DCS data, may be sampled at frequencies of up to 500 Hz, although higher frequencies may be possible. Again, this stands in contrast to traditional DCS systems and methods that, for example, have a sampling time for DCS measurements of approximately 1.5 seconds or longer. As described herein, the systems and methods of the present disclosure acquire DCS measurements at a temporal resolution greater than a pulsatile frequency of cerebral blood flow of the subject. As such, the pulsatile information can be determined from the DCS data.

The controller 610 may be further configured to analyze acquired data, including DCS data and physiological data, in order to provide estimates of quantities, such as ICP, and others, as described. For instance, the controller 610 may be configured to analyze autocorrelation curves at various timescales to determine a blood flow, at various points within a cardiac cycle. In addition, the controller 610 may combine DCS data acquired over a number of cycles, the DCS data being acquired at specific time points or over a range of time points in the cardiac cycle.

Individual measurements may or may not have sufficient signal to noise ratio (SNR) for analysis of desired parameters such as CrCP, ICP, CPP, CVR, and others. As such, a measurement taken from one cardiac cycle can be averaged with a measurement from a different cardiac cycle, while ensuring proper gating of the signals. That is, individual measurements could be timed to exactly coincide with the same portion of the cardiac cycle, or the measurements could be asynchronous to the cycle resulting in an equivalent time average. Equivalent time averaging has superior sampling of the cycle, but either method can be used. In addition to the cycle average, the same data can be averaged over longer times. In this manner, both pulsatile and average blood flow, for example, may be provided. Alternatively, or additionally, the controller 610 may integrate or combine data acquired over an entire cardiac cycle.

In some aspects the controller 610 may be configured to determine a condition of the subject based on determined parameters, such as intracranial pressure, and others. For example, the controller 610 may be configured to determine a risk of cerebral ischemia, or a loss of autoregulation and/or regulatory reserve. In addition, the controller 610 may also be configured to determine an effectiveness of an administered treatment using determined physiological parameters, such as intracranial pressure.

The controller 610 may be further configured to generate and provide a report to a user. The report may include a variety of information including, real-time or intermittent physiological signals or measured quantities, such as ICP, as well as other clinically relevant parameters, including cerebral perfusion pressure (CPP), cerebrovascular resistance (CVR), vessel wall tone, cerebral blood flow-cerebral spinal fluid pulsatility coupling and cerebral compliance, dynamic autoregulation, cerebral perfusion reserve, and other parameters or quantities generated therefrom. Provided signals may be in the time domain, as time series, as well as the frequency domain, as power spectra.

The report may also indicate a condition of the subject being monitored, as well as other information associated with the subject. For instance, the report may indicate a risk for a cerebral ischemia, or a loss of autoregulation or regulatory reserve. The report may further include an audio and/or visual alarm to indicate an acute condition, such as when one or more estimated quantities exceed a safe threshold, or a risk for complications is increased. For example, an alarm may provided when an estimated ICP is in a range between 11 and 20 mmHg, between 21 and 40 mmHg, and greater than 40 mmHg. The alarm signal may also adapt depending on the severity of the risk or the magnitude of the quantity.

Figure 8:
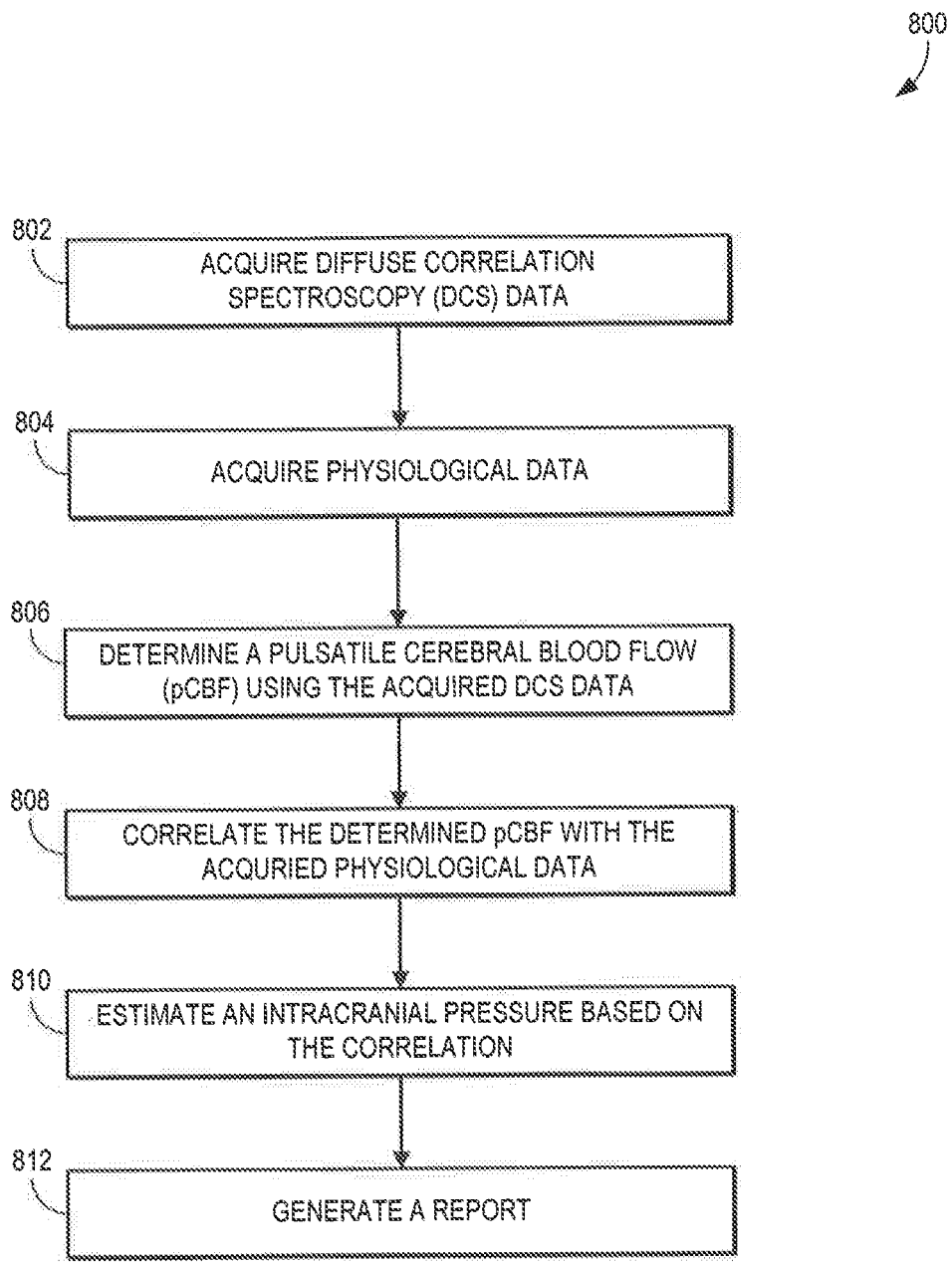
FIG. 8 is a flowchart setting forth steps of a process in accordance with aspects of the present disclosure.
Figure 9:
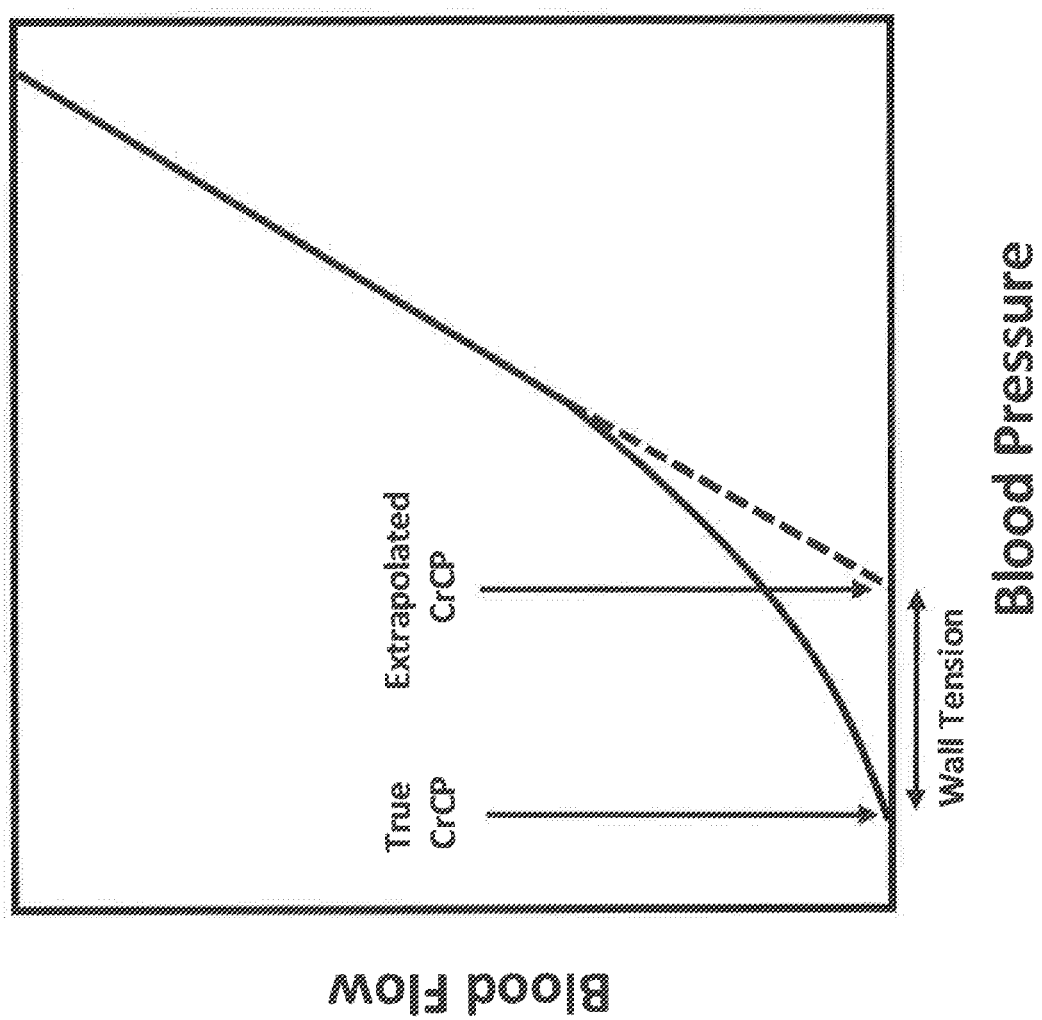
FIG. 9 is a graph showing how the critical closing pressure is influenced by wall tension.

Referring now to FIG. 8, the steps of a process 800 in accordance with aspects of the present disclosure are described. The process 800 may be carried out on any system or apparatus, such as the one described with reference to FIG. 6. As shown in FIG. 8, the process 800 may begin at process blocks 802 and 804 with acquiring DCS and physiological data using various sensors placed about a subject. The data acquired at process blocks 802 and 804 may be obtained in any number of ways, as described, including intermittently or continuously. For instance, in some aspects, DCS data may be acquired at multiple times within a cardiac cycle. Example physiological data includes electrocardiogram (ECG) data, electroencephalogram (EEG) data, near infrared spectroscopy (NIRS) data, blood pressure data, respiratory data, hemoglobin data, pulse oximetry data, and combinations thereof.

The data acquired at process blocks 802 and 804 may also be processed in any number of ways. For instance, depending upon the requisite signal to noise ratio (SNR), data acquired over a number of cardiac cycles may be combined or averaged. In particular, the acquisition and averaging of DCS data does not need be limited to fixed correlation curves. Specifically, photon count data, whether a simple number of counts per time interval or the number of time intervals between photon detection, can be processed and averaged for cycles and events. For example, the photon data over short periods within the cardiac cycle can be used to calculate correlation curves and perform cycle averaging. The same photon data can be used with data over a longer time to calculate the correlation curve on the time scale of another period of interest (e.g. steady-state average, respiration, etc.). This approach can be used for non-cyclical events as well. For example, the blood flow associated with periods of time before and after a distinct EEG event such as a burst or seizure. Gating and averaging can be performed prospectively and/or retrospectively.

At process block 806 a pulsatile cerebral blood flow may be determined using the acquired DCS data. In particular, this step may include generating autocorrelation curves at various timescales using obtained photon counts and analyzing such curves to determine a blood flow, at various points within a cardiac cycle. In some aspects, a steady cerebral blood flow may also be determined at process block 806.

Referring again to FIG. 8, the determined cerebral blood flow may then be correlated with acquired physiological data, as indicated by process block 808. In some aspects, the determined pulsatile cerebral blood flow (pCBF) can be correlated with pulsatile arterial blood pressure (pABP). Other correlations may also be determined at process block 808.

Then, as indicated by process block 810, an intracranial pressure may then be estimated based on correlation. As such, a critical closing pressure may be computed to estimate the intracranial pressure. Other parameters may also be estimated at process block 810 using the DCS data and physiological data, as described. For example, cerebral perfusion pressure, vessel wall tone, cerebral blood flow-cerebral spinal fluid pulsatility coupling, cerebral compliance, dynamic autoregulation, cerebral perfusion reserve, cerebrovascular resistance, oxygen saturation, hemoglobin concentration, cardiac output, stroke volume, brain activity, cardiac activity, and various combinations or changes thereof, may be determined at process block 810. In some aspects, the characteristics of a pulsatile pressure-flow relationship curve, as described with reference to FIG. 3, for instance, may also be used to determine desired physiological parameters.

In some aspects, a condition of the subject based on determined parameters, such as ICP, and others, may be determined at process block 810. For example, a risk of cerebral ischemia, or a loss of autoregulation and/or regulatory reserve may be determined. In other aspects, an effectiveness of an administered treatment may be determined using determined physiological parameters, such as intracranial pressure.

Then, at process block 812 a report, of any form, may be generated and provided to a user. The report may include a variety of information including, real-time or intermittent values of measured physiological parameters or quantities, such as ICP, blood flow, as well as other clinically relevant parameters, including cerebral perfusion pressure (CPP), cerebrovascular resistance (CVR), vessel wall tone, cerebral blood flow-cerebral spinal fluid pulsatility coupling and cerebral compliance, dynamic autoregulation, cerebral perfusion reserve, and other parameters or quantities generated therefrom. The report may also identify a condition of the subject being monitored, as well as other information associated with subject. For instance, the report may indicate a risk for a cerebral ischemia, or a loss of autoregulation or regulatory reserve.

As described, FIG. 7 shows an example of how the photon counts can be correlated in reference to another signal or event at one or more timescales. Specifically, FIG. 7 shows ECG data 702 and DCS data 704 as a function of time. In particular, the DCS data 704, in the form of a stream of photon counts, can be parsed, in either synchronous, partially synchronous, or asynchronous manner, with regards to another physiological signal, such as ECG data 702, to generate one or more correlations functions 706. Such parsing may be achieved with reference to other physiological signals, including ECG, EEG, NIRS, or other physiological signals. Thus, the same data could be combined with regards to multiple events with the appropriate time and duration for each signal. For example, the same signal could process blood flow with regards to cardiac cycle from an ECG and flow before and after a seizure event recorded in EEG. Different time scales could be used between different signals or within the same signal, including, but not limited to, determining both pulsatile and steady flow.

In some aspects, intra-cardiac cycle and intra-respiratory cycle flows, gated by appropriate cardiac and respiratory signals, may be calculated at two different timescales within the ECG. In others, cardiac cycle timing could be determined from a blood pressure sensor or the optical signals themselves. The timing and duration could be fixed or dynamically and/or algorithmically determined, either in real-time, near-real time, or in post-processing. For example, the DCS data 704 could be parsed on a cycle-by-cycle basis, following the spontaneous changes in heart rhythm. The processing may include other transformations, for example a temporal offset to account for the difference in phase between an ECG signal and the CBF signal to account for the transit time of blood from the heart to the brain, and/or other instrument factors The processing could be performed either in software (for example, using FFTs, etc.), in hardware (for example, multi-tau algorithm, FFT, etc.), or any combination thereof.

Figure 10:
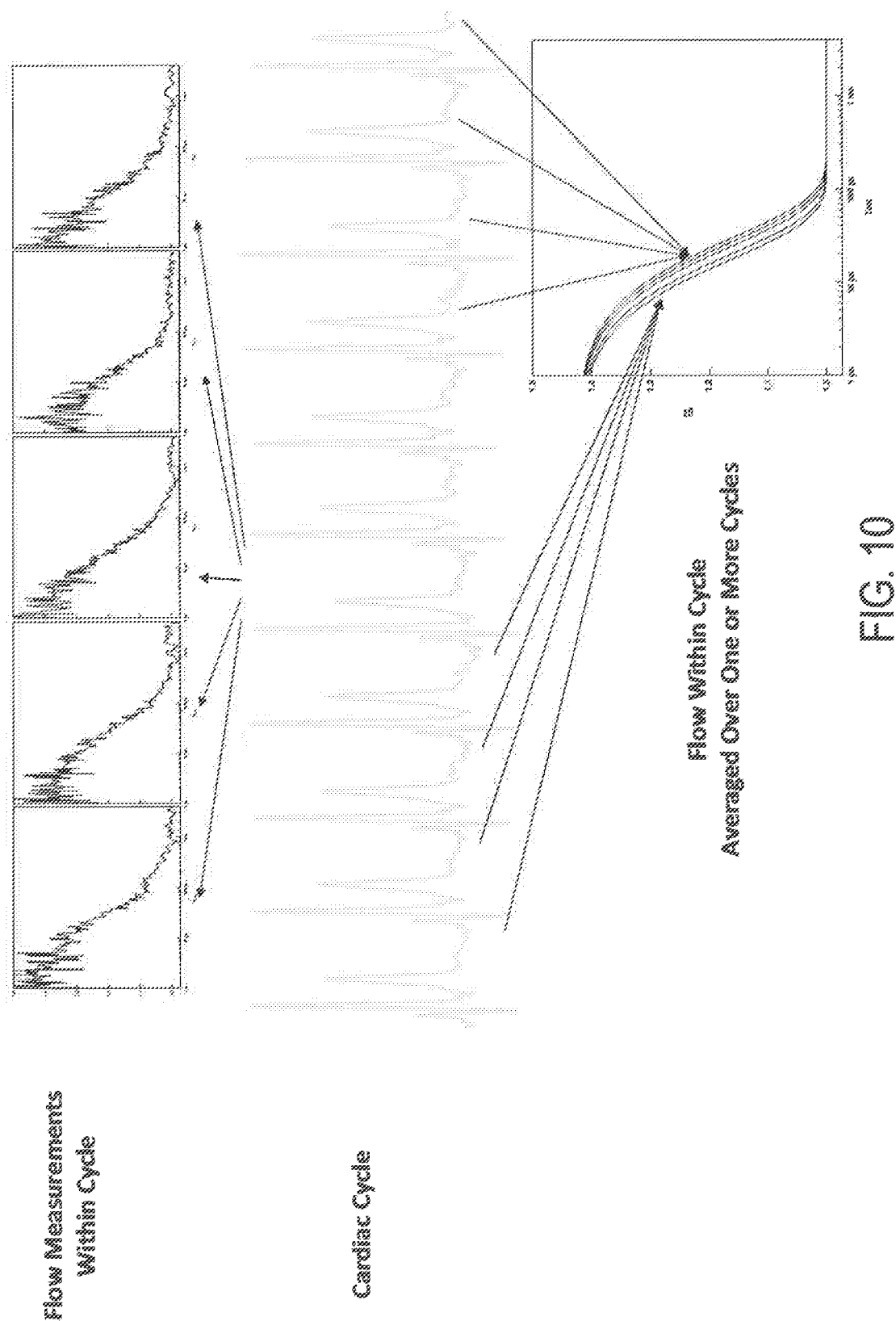
FIG. 10 is a graphical illustration showing acquisition, gating, and averaging of pulsatile diffuse correlation spectroscopy (pDCS) data.

By way of example, FIG. 10 shows pulsatile blood flow measurements obtained from a human subject in accordance with aspects of the present disclosure. In this example, flow measurements were acquired in an integration time less than the period of a cardiac cycle with a hardware correlator, as described with reference to FIG. 6. As described, in some aspects, flow measurements may be inter-cycle combined, processed, and/or averaged with equivalent intra-cycle measurements. In this manner, the signal-to-noise ratio (SNR) and/or intra-cycle time resolution may be increased. The amount of combination can be set by a predetermined amount, such as time, number of samples and so forth, or determined dynamically and/or algorithmically, such as when a desired SNR is achieved, or when number of intra-cycle points are acquired. Measurements may also be combined, processed, and/or averaged with or without regard to the cycle in which they were acquired, and may be used for determining a baseline.

Figure 11A:
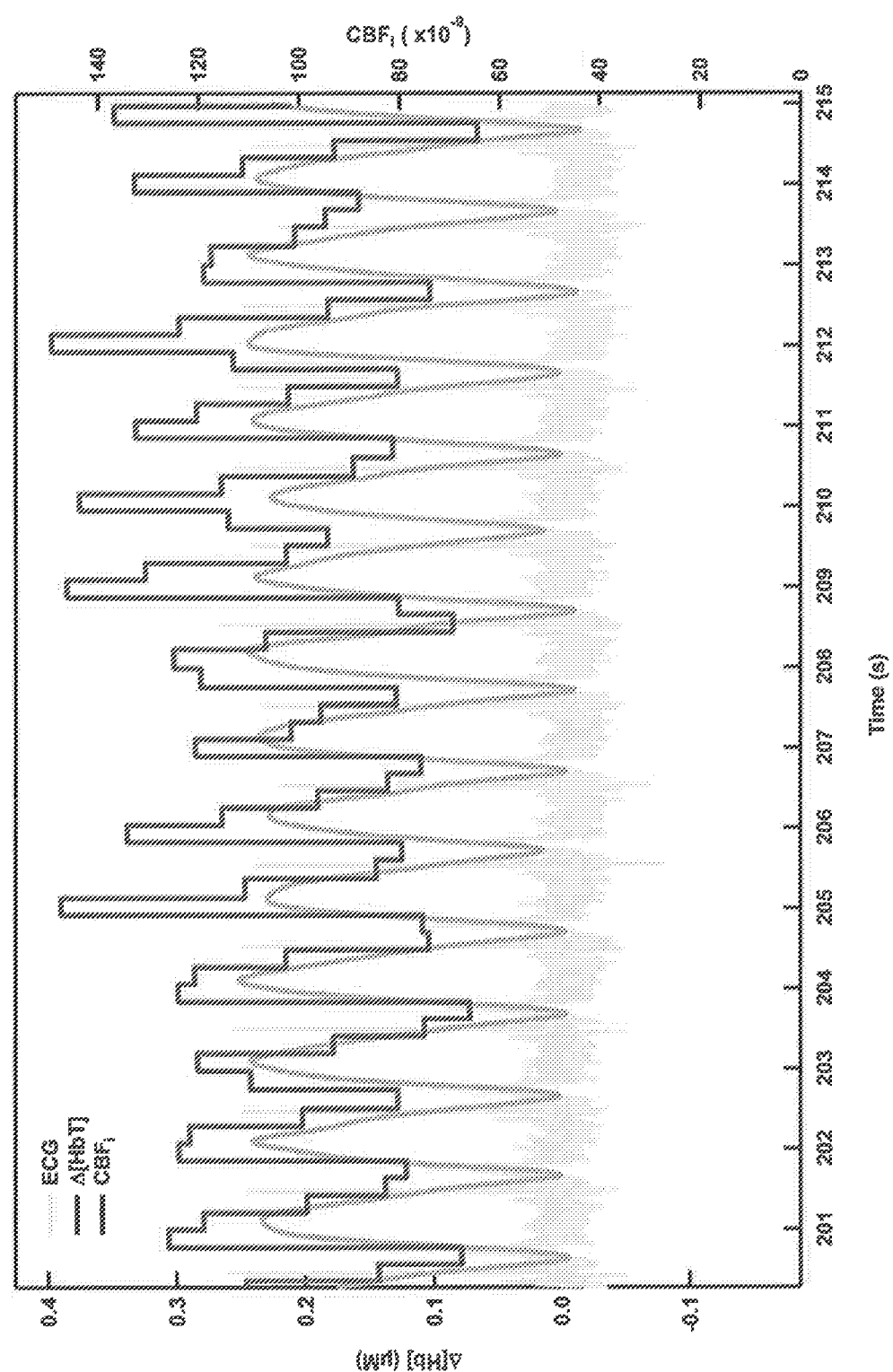
FIG. 11A is a graph showing simultaneous electrocardiograph (ECG), near infrared spectroscopy (NIRS) and pDCS data.
Figure 11B:
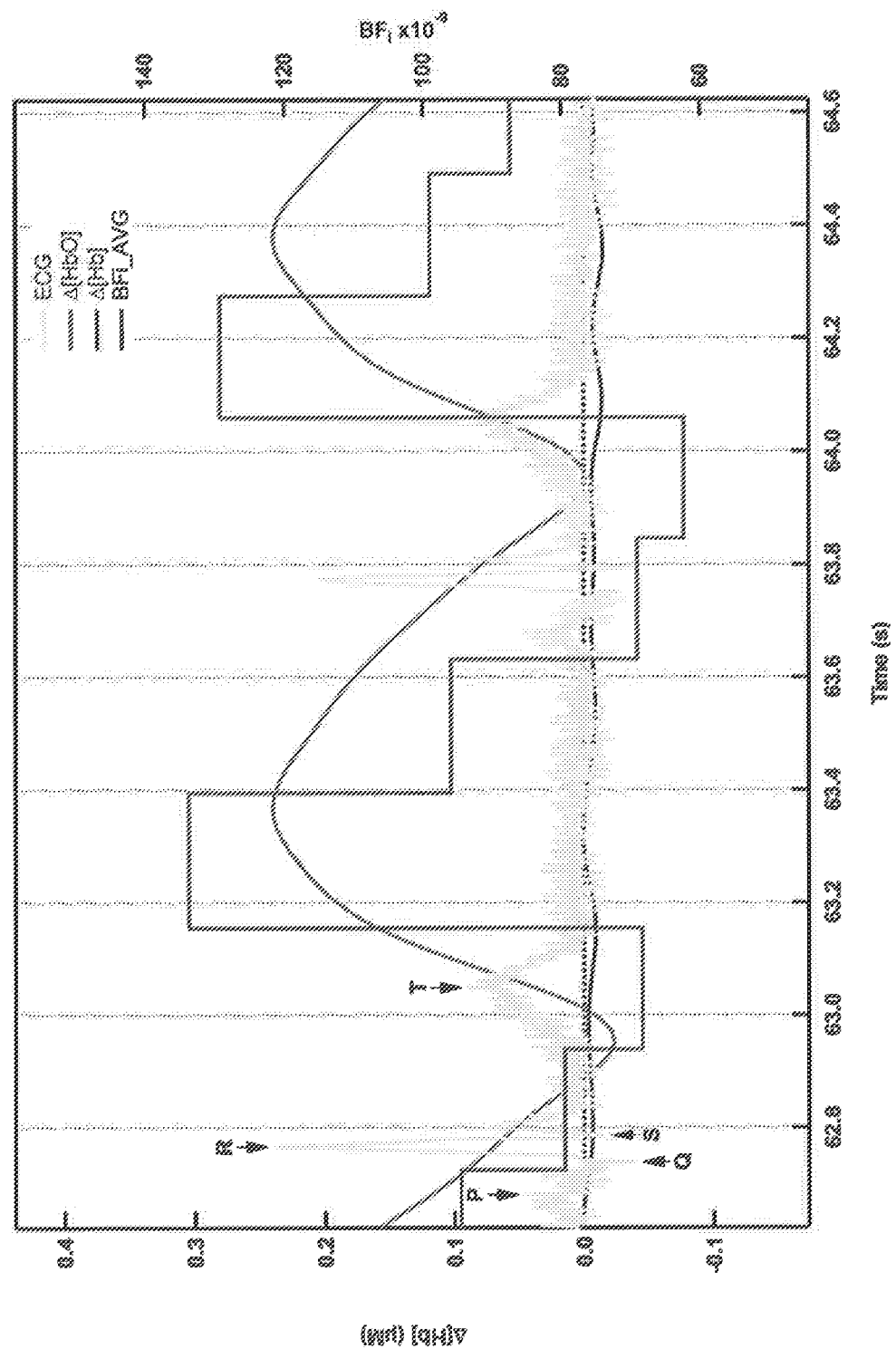
FIG. 11B is another graph showing simultaneous ECG, NIRS and pDCS data.

As another example, FIGS. 11A and 11B demonstrate simultaneous measurements of pulsatile DCS with ECG and CW NIRS. As can be seen, the DCS data has a temporal resolution of 4-5 samples per second. The NIRS and DCS data were collected from an integrated optical probe place on the forehead to sample the same tissue in the cortex. ECG was recorded from two leads placed on the chest of the subject. Although the data points were acquired asynchronously, the pulsatile blood flow, hemoglobin concentration changes and cardiac electrical activity were all physiologically synchronous. However, due to transit time differences between the heart beat and arrival of blood in the cortex, there was a phase difference between the ECG/NIRS signals and the ECG activity. In general, such phase difference could be accounted for by calibration and/or processing.

Figure 11C:
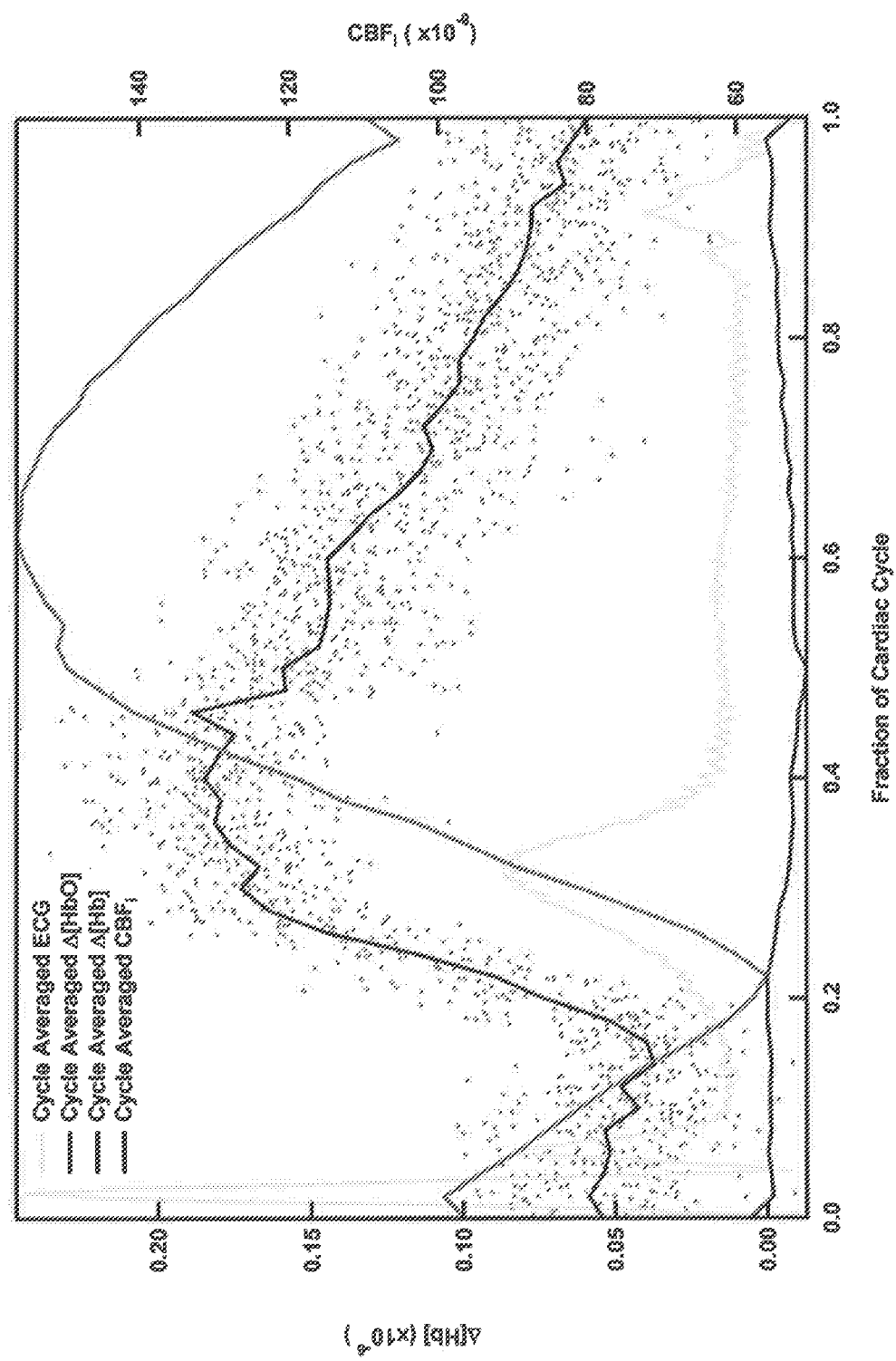
FIG. 11C is graph showing asynchronous cardiac cycle averaging.

As yet another example, FIG. 11C shows the results of cycle averaging. Specifically, a portion of the data from FIGS. 11A and 11B was averaged over the cardiac cycle in an equivalent time average. Further processing can be performed to perform calibrations and/or extract relevant parameters from the data.

Figure 12:
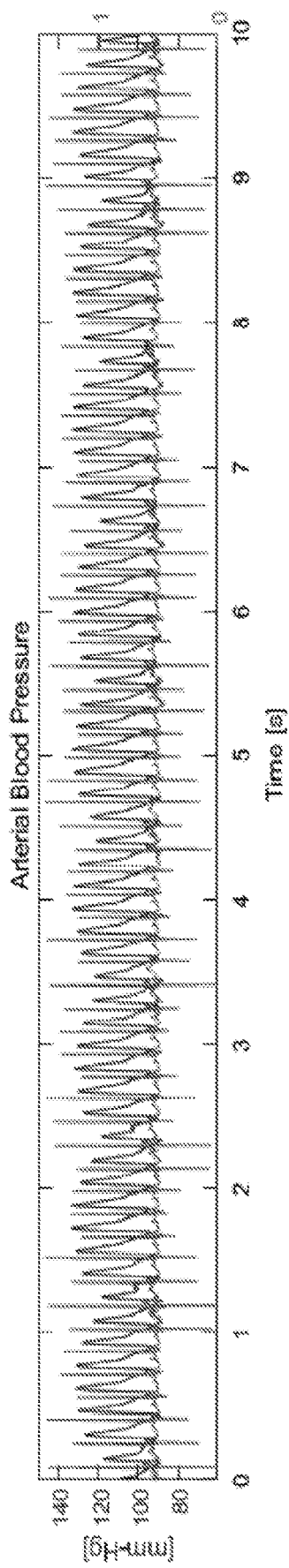
FIG. 12 are graphs showing arterial blood pressure, intracranial pressure, and blood flow based on DCS data, simultaneously measured in an anesthetized rat.
Figure 12:
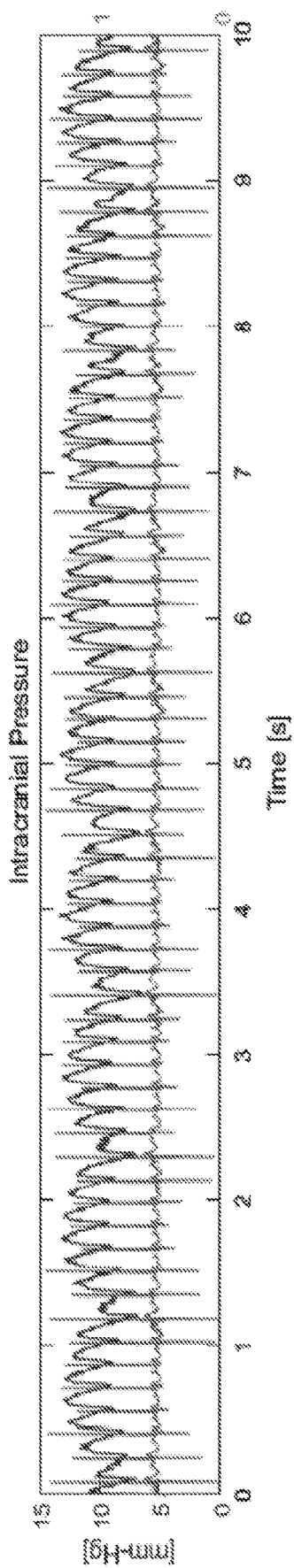
Figure 12:
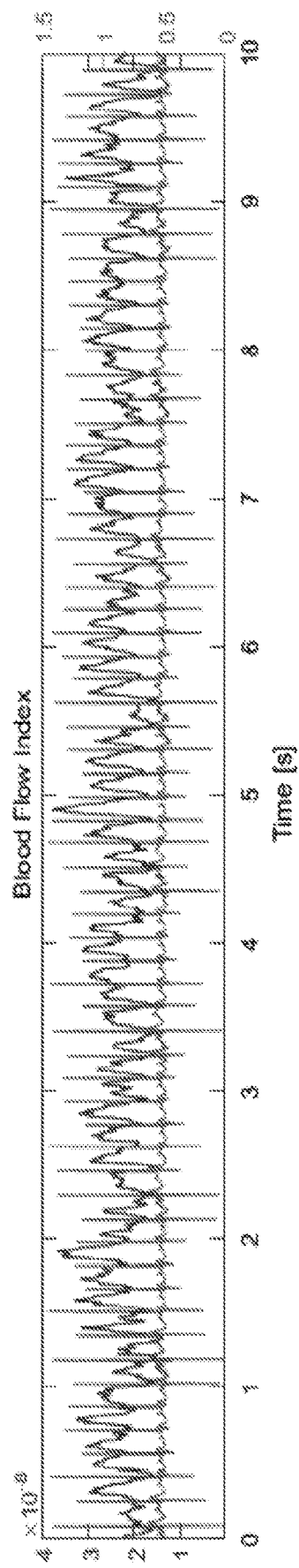

In yet another example FIG. 12 shows a segment of data acquired from an anesthetized rat. Specifically, arterial blood pressure, intracranial pressure (acquired with a fiberoptic transducer inserted in a rat's brain), and blood flow measured with DCS were simultaneously measured. In this example, flow measurements were acquired from a stream of photons and correlated using software, as described with reference to FIG. 6. These results demonstrate that the present approach can resolve the faster pulsatile flows of small mammals. This fast speed is important because it enables: 1) use in animal models for biomedical research, 2) better temporal resolution of the cardiac cycle in adults, 3) sufficient resolution for premature and full-term infants, 4) resolution for patients with cardiac defects. Furthermore, the data in FIG. 12 shows sensitivity to pulsatile and respiratory variations in cerebral blood flow.

As described, the ICP can be derived by estimating the critical closing pressure (CrCP). That is, the ICP can be derived by estimating the value of arterial blood pressure at which cerebral blood flow approaches zero, such as can be derived as detailed with reference to FIG. 3. The use of CrCP as a substitute for ICP is based on the following concept. Specifically, the relationship between flow and pressure in a uniform cylindrical vessel of length L and radius r, is given by Poiseuille's law, which by analogy with Ohm's law, can be written as:

$$F = \frac{(P_i - P_o)}{CVR} \quad (3)$$

here F is flow, $P_i$ and $P_o$ are the inflow and outflow pressures, and the resistance is $$CVR = \frac{\delta \mu L}{\pi r^4} \quad (4)$$

with blood viscosity, $\mu$. In a simplified model of a collapsible cortical vessel with zero active tension, $P_i$ is equal to ABP, and at equilibrium, if the intracranial pressure is greater than the venous pressure, $P_o$ is equal to ICP. When ABP approaches $P_o$, blood flow ceases, implying CrCP is equal to ICP. In a more realistic description of the flow-pressure relationship, one needs to include the effects of active wall tension and vessel elasticity:

$$CrCP = ICP + T_{wall} \quad (5)$$

Models based on Laplace's law, including a non-linear elastic curve and a radius-dependent active tension, show that CrCP depend both on ICP and on the vasomotor tone, and that ICP is lower than the CrCP estimates that use a simple linear regression of the pressure-axis intercept (FIG. 8). From either the non-linear, linear CrCP, or a combination of the two, the wall tension can be determined and provide information about chronic and acute vessel physiology and pathology.

CrCP can provide a superior estimate of ICP compared with traditional pulsatility index (PI) computations, because CrCP is determined from measurements of both the driving arterial blood pressure and the flow response. By contrast, PI is estimated purely from flow velocity. Thus, the present disclosure allows for some of the physiological factors influencing PI to be eliminated in determining CrCP. This makes CrCP a more robust measure.

As described, blood flow velocity measurements based on transcranial Doppler ultrasonography have been used to estimate CrCP. However, while these estimates can correlate with invasive ICP values, they do not reach an acceptable confidence interval to be clinically useful. In fact, while theoretically estimated CrCP should be higher than ICP according to Eqn. 5 above, both higher and lower values were measured by transcranial Doppler ultrasonography. Since in these experiments arterial blood pressure (ABP) measurements are performed using standard arterial lines, the variability in the transcranial Doppler ultrasonograph estimation of ICP is hence driven by the known issues with this approach.

Moreover, transcranial Doppler ultrasonography measures flow velocity and not blood flow, which depends on the cross-sectional area of the imaged vessel. Also, flow velocity is measured on a section of the middle cerebral artery, which is a large vessel with high wall tension and elasticity that is only indirectly impacted by changes in ICP.

By contrast, the present approach utilizes DCS data, providing a better estimate of CrCP compared to previous techniques. This is because DCS measures blood flow and not blood flow velocity. In addition, measurement of pulsatile cerebral blood flow using DCS, in accordance with the present disclosure, is directly sensitive to small cortical arterioles, venules and bridging vessels, which due to their small transmural pressure determine the vasomotor tone of the cerebral circulatory system, and hence are critically impacted by changes in ICP.

In addition to ICP, other parameters may also be estimated. One non-limiting example includes CPP, defined as the mean arterial pressure minus the critical closing pressure:

$$CPP = MABP + CrCp \quad (6)$$

Autoregulation maintains constant CBF across a large range of CPP (50 to 150 mmHg). Reductions of CPP below the lower limit of autoregulation causes CBF to become pressure passive and arteries and arterioles to passively vasodilate. The present approach can hence detect and warn of risk of this condition. Hypotension has adverse consequences for patients with traumatic brain injury and guidelines are to maintain CPP above 50-70 mmHg. Currently, CPP is estimated from invasive ICP measures as a proxy for CrCP in the equation above. The ability to continuously and noninvasively monitor CPP at the bedside would impact the management of a larger number of patients than currently done with invasive measures.

As another example, since blood flow, rather than flow velocity is measured in arterioles, cerebrovascular resistance can be estimated (FIG. 3):

$$CVR = \frac{\Delta pABP}{\Delta pCBF} \quad (7)$$

By simultaneously and continuously measuring both changes in CPP and CVR, cerebral autoregulation can be non-invasively monitored at the bedside. Failure of autoregulation is associated with a worse outcome in various acute neurological diseases.

As may be appreciated, CrCP, ICP, CPP and CVR are tremendously important parameters for the diagnosis and management of patients under many clinical situations, including but not limited to, critical care such as infant, pediatric, or neuro intensive care units, anesthesia and/or surgery, emergency and trauma wards, recovery wards, post intensive care, battle fields, spacecrafts, extreme environments, during sports or on the sidelines, disaster or accident sites, etc. The present approach of measuring pulsatile flow allows estimation of these parameters continuously and non-invasively at the bedside, on an outpatient and/or home care basis. Information generated from such monitoring can be used to understand, for example, the complex pathophysiology after traumatic brain injury, better target care, identify new therapeutic opportunities, and, in general, substantially improve neurocritical care management.

Several approaches can be used to estimate autoregulatory capacitance. A moving correlation coefficient between $CBF_i$ and/or CVR and CPP and/or AP can quantify autoregulation status, with a correlation near one during impaired autoregulation during pressure passive hypo- or hyperemia and near zero for intact autoregulation. Another approach may include, but is not limited to, directly measuring changes in CBF and/or CVR with changes in AP and/or CPP, either spontaneously or induced correlation of CBF and/or CVR fluctuations and changes with CPP and/or AP, correlation of the variances of CBF and/or CVR with CPP, cross-spectral coherence and gain analysis between CBF and/or CVR and CPP and/or AP, phase shifts between CBF and/or CVR with changes in AP, CPP, and/or CBV. In some aspects, a change in blood pressure can arise spontaneously, or be induced by external means such as leg-cuff release, or other means.

In some aspects, the PI may be computed. In particular, the PI is proportional to ICP and can be used to monitor changes in ICP. The PI can be calculated from $pCBF_i$ directly using the following equation:

$$PI = \frac{\text{systolic } CBF_i - \text{diastolic } CBF_i}{\text{mean } CBF_i} \quad (8)$$

PI can also be determined in the frequency domain using the harmonic components of $CBF_i$. In some implementations, pulsatile DCS (pDCS) PI can be used when measurements of blood pressure are not available. PI may also have greater sensitivity to ICP changes at low intra-cranial pressures, even when blood pressure signals are measured.

When blood pressure measurements are obtained in conjunction with pDCS measurements, a pressure-flow relationship, as described with reference to FIG. 3 can be obtained. Such a pressure-flow relationship may then be analyzed to generate a wide variety of information, including but not limited to, a zero flow pressure or CrCP, CPP, CVR, wall tension, and so forth. It is estimated that approximately 11 million photons would provide a precision of +/−5 mmHg in measurement of CrCP using the linear model. The photon flux in the adult measurement described with reference to FIGS. 11A and 11B was approximately 200,000 counts per second, and included an integration time of about 1 minute. The required integration time could be further decreased with the use of additional detectors. Thus, the present approach is feasible from a practical standpoint. However, this disclosure is not limited to a specific number of detected photons. Other criteria for precision, accuracy or quality can be used. These metrics can be calculate online or in post-processing. They could also be used to dynamically adjust the measurement process, optimizing signal quality and dynamic response.

In some implementations, CrCP, and other parameters can be estimated by other analysis methods, including, but not limited to the application of transfer function, correlation, coherence, frequency, or time-domain analyses of pDCS. These analyses may be performed individually or together, in whole or in part, with or without taking into consideration other physiological measurements such as BP, ICP, ECG, EEG, and others.

For example, CPP can be estimated using an analysis of the frequency spectra of blood pressure and $CBF_i$. Specifically, from the first harmonics, CPP can be estimated according:

$$CPP = \frac{A1}{CBF_i 1} \times \text{mean } CBF_i \quad (9)$$

where A1 and $CBF_i 1$ are the first harmonics of arterial pressure and pCBFi, respectively. From CPP, CrCP can be approximated using:

$$CrCP = BP - \frac{A1}{CBF_i 1} \times \text{mean } CBF_i \quad (10)$$

Also, CPP can also be approximated by $$CPP = MAP \times \frac{\text{diastolic } CBF_i}{\text{mean } CBF_i} + \text{Constant} \quad (11)$$

Furthermore, CCP may be estimated using a linear interpolation from diastolic and systolic values of $CBF_i$ and BP. Many other such combinations can be utilized.

In some aspects, CrCP can be estimated from pDCS and different types of blood pressure monitors. For example, arterial pressure can be measured invasively through sensors with an invasive arterial line. CrCP estimated in this way is semi-invasive because, while the blood pressure measurements are invasive, the pDCS measurement remains non-invasive. In this case, although the BP measurement is invasive, this approach is still a significant improvement compared to current techniques, since an arterial line is considerably less invasive than a cranial bolt or burr hole, as required for conventional ICP sensors. In addition, the risk of complications for an arterial line is low and they are routinely used in critical care situations. Furthermore, use of ICP monitoring is much more restricted than arterial line due to the higher risks of invasive intracranial probes. Therefore, it may be appreciated that the present approach provides a considerable advancement over the current state of the art because it allows, for the first time, routine measurement and/or monitoring of ICP in a large population of patients receiving arterial lines.

In other aspects, the present approach can also be utilized entirely non-invasively in patients and subjects in general by combining pDCS with non-invasive means to measure blood pressure. For example, absolute pulsatile blood pressures can be measured non-invasively using devices such as the Finapres monitor. Another example includes combining a relative pressure transducer for pulse measurement (for example a simple transducer wrapped to a finger with a bandage) with intermittent absolute measurements by non-invasive means via a sphygmomanometer. This approach provides a considerable advancement over the current state of the art because it extends measurement and/or monitoring of ICP to anyone. In addition, this approach enables measurements in patients whose perceived risk of abnormal ICP does not currently justify measurement by invasive means. Furthermore, patients believed not to be at risk for abnormal ICP, or even with healthy subjects in natural environments, may also be monitored.

There is a consensus that clinically useful ICP measurements are preferred to have an accuracy of at least 10 mm Hg, or less. The precision of $BF_i$ in a DCS measurement is determined by photon statistics. Thus, with a few assumptions and simplifications, an estimate can be obtained for how long the DCS measurements must be integrated to determine the critical closing pressure (CrCP) to within 10 mm Hg.

Assuming a linear relationship between pulsatile blood flow and pressure during the cardiac cycle, namely:

$$F = a + bP \qquad (12)$$

Real measurements may use more complicated models for the flow-pressure relationship (i.e. with wall tension, etc.) but the linear model is sufficient for estimating integration times. Analysis with more realistic models will not require significant differences integration times.

Observations are pairs $(P_i, F_i)$ representing instantaneous blood pressure and flow, with the instantaneous flow measurement having a variance of $\sigma_i$ for each observation. For DCS, $\sigma_i$ is known from photon statistics and the total number of detected photons integrated in a measurement. For ICP determinations, flow can be measured a number of times within the cardiac cycle, with multiple cardiac cycles integrated to achieve sufficient accuracy. In this case, total number of photons refers to the number of detected photons for a measurement within the cardiac cycle after integrating one or more cardiac cycles.

The uncertainty of the maximum likelihood estimation of a and b are then:

$$\sigma_a^2 = \frac{1}{\Delta} \sum_i \frac{P_i^2}{\sigma_i^2} \qquad (13)$$

$$\sigma_b^2 = \frac{1}{\Delta} \sum_i \frac{1}{\sigma_i^2} \qquad (14)$$

where $\Delta$ is defined as:

$$\Delta = \sum_i \frac{1}{\sigma_i^2} \sum_i \frac{P_i^2}{\sigma_i^2} - \left(\sum_i \frac{P_i}{\sigma_i^2}\right)^2 \qquad (15)$$

and the uncertainty in P is negligible. For the linear model, the critical closing pressure (CrCP) may be approximated as:

$$CrCP = -\frac{a}{b} \qquad (16)$$

Then the variance of the CrCP can be propagated from the variances in a and b:

$$\sigma_{CrCP}^2 = CrCP^2 \left(\frac{\sigma_a^2}{a^2} + \frac{\sigma_b^2}{b^2} - 2\frac{\sigma_{ab}^2}{ab}\right) = \left(\frac{a}{b}\right)^2 \left(\frac{\sigma_a^2}{a^2} + \frac{\sigma_b^2}{b^2}\right) \qquad (17)$$

where $\sigma_{ab}^2$ is assumed=0.

For a simple estimate, $\sigma_i$ can be approximated as a constant $\sigma_{BFi}$ for all measurements. This is reasonable because the uncertainty in $CBF_i$ depends primarily only on the detected photon flux and very weakly on the value of $CBF_i$. Then, the variances simplify to:

$$\Delta' = N \sum_i P_i^2 - \left(\sum_i P_i\right)^2 \qquad (18)$$

$$\sigma_a'^2 = \frac{\sigma_{BF_i}^2}{\Delta'} \sum_i P_i^2 \qquad (19)$$

$$\sigma_b'^2 = N \frac{\sigma_{BF_i}^2}{\Delta'} \qquad (20)$$

where N is the number of $(P_i, F_i)$ pairs determined within the cardiac cycle.

$$\sigma_{CrCP}'^2 = \left(\frac{a}{b}\right)^2 \left(\frac{1}{a^2}\left(\frac{\sigma_{BF_i}'^2}{\Delta'}\sum_i P_i^2\right) + \frac{1}{b^2}\left(N\frac{\sigma_{BF_i}'^2}{\Delta'}\right)\right) \qquad (21)$$

$$= \left(\frac{\sigma_{BF_i}'^2}{\Delta' b^2}\right)\left(\sum_i xP_i^2 + \frac{a^2}{b^2}N\right)$$

So, solving for $\sigma_{BFi}$ gives $$\sigma_{BF_i}'^2 = \left(\frac{\Delta' b^2}{\sum P_i^2 + \frac{a^2}{b^2}N}\right) \sigma_{CrCP}'^2 \qquad (22)$$

$$= \left(\frac{\Delta' b^2}{\sum P_i^2 + CrCP^2 N}\right) \sigma_{CrCP}'^2$$

Thus, if there is a specific requirement for the accuracy of the zero flow pressure, a physiologically reasonable b and CrCP may be assumed, and a measurement acquisition rate through parameter N can be chosen to estimate the accuracy required for the blood flow measurement. The blood flow accuracy can then be used to determine the minimum number of photons required per blood flow measurement and estimate the required total integration time.

Setting N to be the number of flow determinations through the cardiac cycle allows us to estimate the uncertainty from the extremes of the systolic and diastolic pressures and $CBF_i$. Replacing $P_i$ with a linear model of pressure ranging through systolic to diastolic ($P_s$ to $P_d$):

$$P_i = P_d + \frac{(P_s - P_d)}{(N-1)}i \qquad (23)$$

-continued $$\Delta' = N \sum_{i}^{N \text{ periods during cardiac cycle}} \left(P_d + \frac{(P_s - P_d)}{(N-1)} i\right)^2 - \left(\sum_{i}^{N \text{ periods during cardiac cycle}} \left(P_d + \frac{(P_s - P_d)}{(N-1)} i\right)\right)^2$$

Using (where i and N are consistent with model for $x_i$):

$$\sum_{i}^{N} i = \frac{N(N-1)}{2} \quad (24)$$

$$\sum_{i}^{N} i^2 = \frac{N(N-1)(2N-1)}{6}$$

$\Delta'$ simplifies to:

$$\Delta' = \left(\frac{(N+1)N^2}{12(N-1)}\right)(P_s - P_d)^2 \quad (25)$$

and $\sigma'_{BF_i}$ to:

$$\sigma'^2_{BF_i} = \left(\frac{\Delta' b^2}{NP_d^2 + \left(\frac{N(2N-1)}{6(N-1)}\right)(P_s - P_d)^2 + NP_d(P_s - P_d) + CrCP^2 N}\right) \sigma'^2_{CrCP} \quad (26)$$

From these two equations and assumptions of $P_s$, $P_d$, b, and a nominal value of CrCP, the required accuracy for the DCS measurement ($\sigma'_{BF_i}$) can be estimated from the specified accuracy of the ICP determination ($\sigma'_{CrCP}$). For $P_s$, and $P_d$, a normal systolic blood pressure of 120 mm Hg and diastolic pressure of 80 mm Hg is assumed.

In preliminary pDCS measurements, $CBF_i$ ranged from $7.1 \times 10^{-8}$ to $1.3 \times 10^{-7}$ through the cardiac cycle. The ratio of peak flows appears to be underestimated due to the limited DCS acquisition rate achieved with instrumentation utilized. Thus, the ratio of peak flow in preliminary measurements was only 1.8×, while values of 2.9× were reported in the literature for ratios of peak flow velocities in transcranial Doppler ultrasonography. Presumably, the pDCS peak flow ratio can increase with a faster DCS acquisition.

However, the transcranial Doppler ultrasonography ratio will remain larger since pulsatility is larger in the larger artery measured by transcranial Doppler ultrasonography than in the downstream smaller vessels measured by DCS and because DCS also measures the out flow which is less pulsatile than the inflow. Regardless, the underestimated flow ratios makes this error estimation a worst case condition and the actual accuracy would be expected to be better than this prediction. Using the peak flows from the preliminary measurement, b can be approximated:

$$b = \frac{1.3 \times 10^{-7} - 7.1 \times 10^{-8}}{(120 - 80)} = 1.5 \times 10^{-9} \frac{CBF_i}{\text{mm Hg } BP}$$

Normal CrCP values range from 5 to 10 mm Hg and can elevate to over 50 mm Hg under pathological conditions. Hence CrCP can be estimated with 10 mm Hg as a reasonable nominal value. A DCS acquisition rate of 25 Hz can then be chosen, making N approximately 25.

To meet the clinical target CrCP accuracy of within 10 mmHg, a 99% confidence interval to be +/−5 mmHg is selected. Thus, the required $\sigma'_{CrCP}$ is specified to be $$\sigma'_{CrCP} = \frac{5 \text{ mm Hg}}{2.58} = 1.94 \text{ mmHg}.$$

Utilizing the assumed values into the equations for $\Delta'$ and $\sigma'_{BF_i}$ determines that a total SNR of approximately 42 is required for each of the 25 flow determinations within the cardiac cycle. From the measured DCS SNR curve, about 440 k photons are needed to achieve a $BF_i$ SNR of 42. Thus, approximately 11 million detected photons are required to be integrated across the entire cardiac cycle. In the preliminary measurements, the detected photon flux was about 200 kcps per detector, so 55 seconds of integration would be sufficient for a single detector, or only 18 seconds if all three detectors are averaged together. Thus, though this model does not take into account other sources of error, such as the accuracy of the pressure measurement, it does show that pDCS measurements and CrCP determinations are fundamentally practical from a DCS SNR standpoint.

In summary, the present disclosure overcomes the drawbacks of previous technologies by providing a system and method for accurately and non-invasively monitoring patients. More specifically, the system and method described herein utilize diffuse correlation spectroscopy to measure pulsatile, as well as steady, cerebral blood flow for determining parameters useful in the diagnosis and management of patients.

As may be appreciated from descriptions herein, the present disclosure provides a wide range of applicability. For example, the system and method described can be used to monitor changes in ICP, CVR, CPP, WT, and autoregulation capacity with drugs or anesthetics, as well as provide monitoring and/or diagnostics with pharmacological manipulations include bolus testing. In addition, the present system and method may be applied to monitoring vasospasm or the effect of vasospasm or vasoparalysis, as well as monitoring cortical spreading depression or the effect of cortical spreading depression. The present system and method may also be applied to monitoring hemorrhages, including subarachnoid hemorrhages, and post-hemorrhage monitoring, tumors, hematoma, hydrocephalus, edema, vascular engorgement, hypercapnia, hypoxia, shock, sepsis. Furthermore, the present approach may be used to investigate chronic diseases and conditions such as hypertension, sleep and other apneas, etc. (measurement of pathological chronic changes in vascular tone), as well as hydrocephalus.

The present system and method may be applied to monitor congestive heart failure, blood flow in non-cerebral organs, peripheral vascular disease. In addition, the provided system and method may be utilized in perioperative, intensive and critical care, as well as goal-directed blood pressure support in patients with critical carotid artery stenosis. Furthermore, the present system and method may be utilized in perioperative management of patients undergoing carotid endarterectomy, and in patients with cardiopulmonary bypass, as well as optimization of blood pressure management in patients with traumatic brain injury undergoing neurosurgical or non-neurosurgical procedures.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for non-invasively monitoring intracranial pressure, the system comprising:
    an optical coupling system configured to transmit and receive light signals from one or more locations about a subject;
    an optical processing system configured to generate diffuse correlation spectroscopy (DCS) data at a temporal resolution greater than a pulsatile frequency of cerebral blood flow of the subject using the transmitted and received light signals;
    a computer programmed to:
        receive the DCS data,
            the DCS data being acquired over a plurality of cardiac cycles;
        analyze the DCS data to determine a pulsatile cerebral blood flow by synchronizing and averaging the DCS data from at least two of the plurality of cardiac cycles;
        correlate the determined pulsatile cerebral blood flow with physiological data acquired from the subject;
        compute a critical closing pressure based on the pulsatile cerebral blood flow;
        estimate an intracranial pressure based on the correlation and based on the computed critical closing pressure; and
        generate a report indicative of the estimated intracranial pressure.

2. The system of claim 1, wherein the system further comprises one or more physiological sensors for acquiring the physiological data from the subject.

3. The system of claim 1, wherein the optical coupling comprises DCS sensors, and near infrared spectroscopy (NIRS) sensors.

4. The system of claim 1, wherein the physiological data comprises at least one of electrocardiogram (ECG) data, electroencephalogram (EEG) data, near infrared spectroscopy (NIRS) data, blood pressure data, respiratory data, hemoglobin data, pulse oximetry data, or a combination thereof.

5. The system of claim 1, wherein the computer is further programmed to determine, using the DCS data and physiological data, at least one of a cerebral perfusion pressure, a vessel wall tone, a cerebral blood flow-cerebral spinal fluid pulsatility coupling, a cerebral compliance, a dynamic autoregulation, a cerebral perfusion reserve, a cerebrovascular resistance, an oxygen saturation, a hemoglobin concentration, a cardiac output, a stroke volume, a brain activity, a cardiac activity, or a combination thereof.

6. The system of claim 1, wherein the computer is further programmed to control the optical processing system to generate DCS data using an integration time less than a period of a cardiac cycle.

7. The system of claim 1, wherein the DCS data is acquired during a portion of each cardiac cycle.

8. The system of claim 1, wherein the computer is further configured to determine an effectiveness of an administered treatment using the estimated intracranial pressure.

9. The system of claim 1, wherein the computer is further configured to determine a condition of the subject based on the estimated intracranial pressure.

10. A method for non-invasively monitoring intracranial pressure using a monitoring system, the method comprising:
    acquiring diffuse correlation spectroscopy (DCS) data at a temporal resolution greater than a pulsatile frequency of cerebral blood flow of a subject using one or more optical sensors placed about the subject,
        the DCS data being acquired over a plurality of cardiac cycles;
    determining a pulsatile cerebral blood flow using the acquired DCS data by synchronizing and averaging the DCS data from at least two of the plurality of cardiac cycles;
    correlating the determined pulsatile cerebral blood flow with physiological data acquired from the subject;
    computing a critical closing pressure based on the pulsatile cerebral blood flow;
    estimating an intracranial pressure based on the correlation and based on the computed critical closing pressure; and
    generating a report indicative of the estimated intracranial pressure.

11. The method of claim 10, wherein the one or more optical sensors comprises DCS sensors, and near infrared spectroscopy (NIRS) sensors.

12. The method of claim 10, wherein the method further comprises acquiring the physiological data from the subject using one or more physiological sensors placed about the subject.

13. The method of claim 11, wherein the physiological data comprises at least one of electrocardiogram (ECG) data, electroencephalogram (EEG) data, near infrared spectroscopy (NIRS) data, blood pressure data, respiratory data, hemoglobin data, pulse oximetry data, or a combination thereof.

14. The method of claim 10, wherein the method further comprises determining using the DCS data and physiological data at least one of a cerebral perfusion pressure, a vessel wall tone, a cerebral blood flow-cerebral spinal fluid pulsatility coupling, a cerebral compliance, a dynamic autoregulation, a cerebral perfusion reserve, a cerebrovascular resistance, an oxygen saturation, a hemoglobin concentration, a cardiac output, a stroke volume, a brain activity, a cardiac activity, or a combination thereof.

15. The method of claim 10, wherein the method further comprises controlling an optical processing system to generate DCS data using an integration time less than a period of a cardiac cycle.

16. The method of claim 10, wherein the DCS data is acquired during a portion of each cardiac cycle.

17. The method of claim 10, wherein the method further comprises determining an effectiveness of an administered treatment using the estimated intracranial pressure.

18. The method of claim 10, wherein the method further comprises determining a condition of the subject based on the estimated intracranial pressure.

19. A method for non-invasively monitoring a subject using a monitoring system, the method comprising:
    acquiring diffuse correlation spectroscopy (DCS) data at a temporal resolution greater than a pulsatile frequency of cerebral blood flow of a subject using one or more optical sensors placed about the subject,
        the DCS data being acquired over a plurality of cardiac cycles;

determining a pulsatile cerebral blood flow using the acquired DCS data by synchronizing and averaging the DCS data from at least two of the plurality of cardiac cycles;

correlating the determined pulsatile cerebral blood flow with physiological data acquired from the subject using physiological sensors;

computing a critical closing pressure based on the pulsatile cerebral blood flow;

estimating at least one parameter based on the correlation and based on the computed critical closing pressure; and generating a report indicative of the at least one parameter estimated.

20. The method of claim 19, wherein the at least one parameter comprises at least one of an intracranial pressure, a cerebral perfusion pressure, a vessel wall tone, a cerebral blood flow-cerebral spinal fluid pulsatility coupling, a cerebral compliance, a dynamic autoregulation, a cerebral perfusion reserve, a cerebrovascular resistance, an oxygen saturation, a hemoglobin concentration, a cardiac output, a stroke volume, a brain activity, a cardiac activity, or a combination thereof.

21. The method of claim 19, wherein estimating the at least one parameter comprises analyzing a pulsatile pressure-flow relationship curve.

* * * * *

UNITED STATES PATENT AND TRADEMARK OFFICE
CERTIFICATE OF CORRECTION

PATENT NO. : 11,089,972 B2  
APPLICATION NO. : 15/565044  
DATED : August 17, 2021  
INVENTOR(S) : Jason Sutin et al.

Page 1 of 2

It is certified that error appears in the above-identified patent and that said Letters Patent is hereby corrected as shown below:

In the Specification

Column 19, Eq. (13), Line 45, "$\sum_i$" should be --$\sum_i$--.

Column 19, Eq. (14), Line 48, "$\sum_i$" should be --$\sum_i$--.

Column 19, Eq. (15), Line 55, "$\Delta = \sum \frac{1}{\sigma_i^2} \sum \frac{P_i^2}{\sigma_i^2} - \left(\sum \frac{P_i}{\sigma_i^2}\right)^2$" should be --$\Delta = \sum_i \frac{1}{\sigma_i^2} \sum_i \frac{P_i^2}{\sigma_i^2} - \left(\sum_i \frac{P_i}{\sigma_i^2}\right)^2$--.

Column 20, Eq. (18), Line 18, "$\Delta' = N\sum P_i^2 - \left(\sum P_i\right)^2$" should be --$\Delta' = N\sum_i P_i^2 - \left(\sum_i P_i\right)^2$--.

Column 20, Eq. (19), Line 21, "$\sum_i$" should be --$\sum_i$--.

Column 20, Eq. (21), Line 32, "$\sum_i$" should be --$\sum_i$--.

Column 20, Eq. (21), Line 35, "$\sum_i$" should be --$\sum_i$--.

Signed and Sealed this  
Fifth Day of October, 2021

Drew Hirshfeld  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 11,089,972 B2

Column 21, Eq. (23), Line 4, "$\sum_{i}^{N \text{ Periods during cardiac cycle}}$" should be --$\sum_{i}^{N \text{ periods cardiac cycle}}$--.

Column 21, Eq. (23), Line 8, "$\sum_{i}^{N \text{ Periods during cardiac cycle}}$" should be --$\sum_{i}^{N \text{ periods cardiac cycle}}$--.